(12) United States Patent
Lee et al.

(10) Patent No.: US 7,531,608 B2
(45) Date of Patent: May 12, 2009

(54) TRANSITION METAL COMPLEXES, CATALYST COMPOSITIONS CONTAINING THE SAME, AND OLEFIN POLYMERIZATION USING THE CATALYST COMPOSITIONS

(75) Inventors: Choong Hoon Lee, Daejeon (KR); Eun Jung Lee, Daejeon (KR); Seungwhan Jung, Suwon (KR); Jong Joo Ha, Daejeon (KR); Beomdoo Seo, Daejeon (KR); Bun Yeoul Lee, Suwon (KR); Ui Gab Joung, Suwon (KR); Dae June Joe, Bucheon (KR)

(73) Assignee: LG Chem, Ltd. (KR)

( * ) Notice: Subject to any disclaimer, the term of this patent is extended or adjusted under 35 U.S.C. 154(b) by 183 days.

(21) Appl. No.: 11/483,754

(22) Filed: Jul. 10, 2006

(65) Prior Publication Data

US 2007/0010638 A1 Jan. 11, 2007

(30) Foreign Application Priority Data

Jul. 8, 2005 (KR) ................. 10-2005-0061821

(51) Int. Cl.
*C08F 4/42* (2006.01)
*C07F 7/28* (2006.01)

(52) U.S. Cl. .............. 526/160; 526/943; 526/161; 526/172; 526/170; 502/103; 556/51; 556/52

(58) Field of Classification Search ........ 556/52, 556/51; 526/160, 161, 172, 170, 943; 502/103
See application file for complete search history.

(56) References Cited

U.S. PATENT DOCUMENTS

| 5,064,802 | A | 11/1991 | Stevens et al. |
| 5,856,258 | A | 1/1999 | Marks et al. |
| 6,090,739 | A | 7/2000 | Riedel et al. |
| 7,009,014 | B2 * | 3/2006 | Suzuki et al. ......... 526/161 |
| 2004/0242410 | A1 * | 12/2004 | Hanaoka et al. ....... 502/117 |

FOREIGN PATENT DOCUMENTS

| EP | 0 210 615 A3 | 2/1987 |
| JP | 2001158753 | 6/2001 |
| JP | 2003221396 | 8/2003 |
| KR | 1020050028664 | 3/2005 |
| WO | WO 02/02649 A1 * | 1/2002 |
| WO | 03024983 | 3/2003 |
| WO | WO 03/24983 A1 * | 3/2003 |
| WO | 2006057869 A1 | 6/2006 |

OTHER PUBLICATIONS

"Crystalline Syndiotactic Polystyrene," Macromolecules, vol. 19, pp. 2464-2465 (1986).
Chien, J.C.W., et al., "Polymerizations of Olefins and Diolefins Catalyzed by Monocyclopentadienyltitanium Complexes Containing a (Dimethylamino) ethyl Substituent and Comparison with ansa-Zirconocene Systems," Journal of Polymer Science, vol. 36, pp. 319-328 (1998).
Nomura, K., et al., "Ethylene/Styrene Copolymerization by Various (Cyclopentadienyl) (aryloxy) titanium (IV) Complexes-MAO Catalyst Systems," Macromolecules, vol. 35, pp. 5388-5395 (2002).
Gibson, V., et al., "Advances in Non-Metallocene Olefin Polymerization Catalysis," Chem. Rev., vol. 103, pp. 283-315 (2003).
Korean Office Action dated May 29, 2007 for Application No. 10-2005-0061821 (All references cited in Office Action are listed above).

* cited by examiner

*Primary Examiner*—Ling-Siu Choi
(74) *Attorney, Agent, or Firm*—Cantor Colburn LLP

(57) ABSTRACT

Provided are a novel transition metal complex where a mono-cyclopentadienyl ligand to which an amine-based group is introduced is coordinated, a method of synthesizing the same, and olefin polymerization using the transition metal complex In the novel transition metal complex, an imino phenyl group is not cross-linked to a metal atom and directly introduced to a cyclopentadiene (Cp) ring. The catalyst composition including the transition metal compound is used to obtain a polyolefin copolymer having a very low density less than 0.910 g/cc.

9 Claims, 1 Drawing Sheet

TRANSITION METAL COMPLEXES, CATALYST COMPOSITIONS CONTAINING THE SAME, AND OLEFIN POLYMERIZATION USING THE CATALYST COMPOSITIONS

CROSS-REFERENCE TO RELATED PATENT APPLICATIONS

This application claims the benefit of Korean Patent Application No. 10-2005-0061821, filed on Jul. 8, 2005, in the Korean Intellectual Property Office, the disclosure of which is incorporated herein in its entirety by reference.

BACKGROUND OF THE INVENTION

1. Field of the Invention

The present invention relates to a novel transition metal complex where a monocyclopentadienyl ligand to which an amine-based group is introduced is coordinated, a method of synthesizing the same, and olefin polymerization using the transition metal complex, and more particularly, to a novel transition metal complex containing a phenylene group that does not form a bridge, a method of synthesizing the same, and olefin polymerization using the transition metal complex.

2. Description of the Related Art

In the early 1990s, Dow Co. developed $Me_2Si(Me_4C5)$ $NtBuTiCl_2$ (Constrained-Geometry Catalyst, hereinafter referred to as CGC) (U.S. Pat. No. 5,064,802). CGC shows excellent properties in a copolymerization reaction of ethylene and alpha-olefin, compared to conventional metallocene catalysts. For example, (1) CGC can be used to form high molecular weight polymers due to its high reactivity at high polymerization temperature, and (2) CGC can be used for copolymerization of alpha-olefin having large steric hindrance, such as 1-hexene and 1-octene. Due to many useful properties, in addition to these properties described above, obtained from use of CGC, research into synthesis of CGC derivatives as a polymerization catalyst is substantially increasing in academic and industrial fields.

For example, synthesis of metal complexes, instead of a silicon bridged CGC, comprising various other bridges and a nitrogen substituent, and polymerization using these metal complexes were performed. Examples of such metal complexes include Complexes 1 through 4 (*Chem. Rev.* 2003, 103, 283).

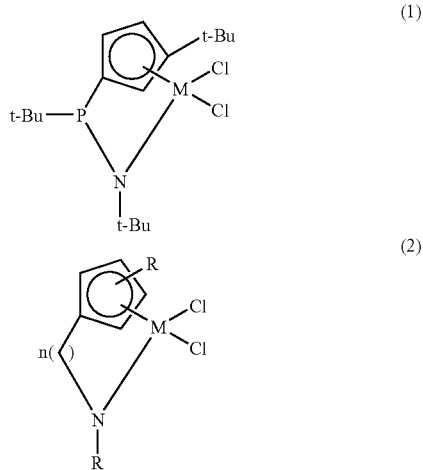

(1)

(2)

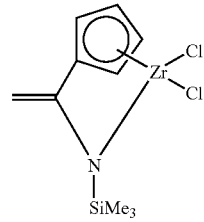

(3)

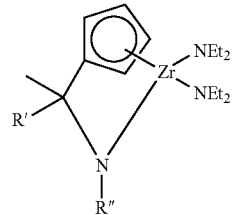

(4)

Complexes 1 through 4 respectively contain a phosphorus bridge, an ethylene or propylene bridge, a methylidene bridge, and a methylene bridge, instead of the silicon bridge of the CGC structure. However, these complexes show low activity or poor copolymerization performance when ethylene is polymerized or when ethylene and alpha-olefin are copolymerized, compared to CGC. Due to these problems, these complexes are difficult to be applied to commercial processes.

On the other hand, only a few kinds of Group 4 transition metal complexes having monocyclopentadienyl ligand at which no bridge is formed were developed for use in ethylene polymerization or copolymerization of ethylene and alpha-olefin. Examples of the transition metal complex having monocyclopentadienyl ligand at which no bridge is formed include $Me_4 CpTiX_2(OAr)$ where X is halide and Ar is aryl, $R_nCpTiX_3$ where R is alkyl, aryl, or a fused ring, and X is halide, alkyl, or alkoxy. Recently, professor Nomura et al. developed $Me_4 CpTiX_2(OAr)$, which is a cocatalyst such as methylalumoxane (MAO), effectively promoting homopolymerization of ethylene and copolymerization of ethylene and 1-hexen (*Macromolecules* 2002, 35, 5388) when being activated. However, compared to $L_1L_2TiX_2$, a piano-stool shaped compound, such as $R_nCpTiX_3$ is unsuitable for polymerization of ethylene or copolymerization of ethylene and alpha-olefin, rather suitable for synthesizing syndiotactic polystyrene (sPS) (European Patent No. 210615 (1987), *Macromolecules* 1986, 19, 2464). In addition, a metal compound prepared by substituting a cyclopentadienyl ring of $R_nCpTiX_3$ with an electron donor, such as $NMe_2$, was developed. However, the metal compound shows a low degree of ethylene homopolymerization activity (*J. Polym. Sci. Polym. Chem.* 1998, 36, 319).

Accordingly, these is a need to develop a catalyst having high polymerizaition performance using a Group 4 transition metal complex having a monocyclopentadienyl ligand at which no bridge is formed.

SUMMARY OF THE INVENTION

The present invention provides a novel transition metal complex in which no bridge is formed.

The present invention also provides a method of preparing the transition metal complex.

The present invention also provides a catalyst composition containing the transition metal complex.

The present invention also provides a method of preparing the catalyst composition.

The present invention also provides a method of preparing a polymer using the catalyst composition.

The present invention also provides a polymer prepared using the method of preparing a polymer using the catalyst composition.

According to an aspect of the present invention, there is provided a transition metal complex of Formula 1:

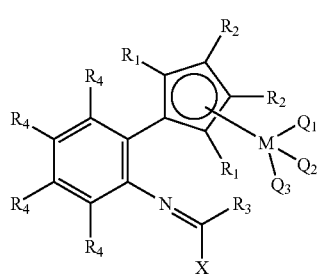

(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group metal substituted with hydrocarbyl, wherein $R_1$ and $R_2$ can be connected by an alkylidine radical that contains a C1-C20 alkyl or aryl radical to form a ring;

$R_4$ is each independently a hydrogen atom; a halogen radical; or a C1-C20 alkyl or aryl radical, wherein two $R_4$ are connected to form a fused ring structure;

$R_3$ is hydrogen atom; a C1-C20 alkyl or aryl radical; or a C1-C20 alkoxy or aryloxy radical;

M is a transition metal of Group 4;

$Q_1$, $Q_2$, and $Q_3$ are each independently a halogen radical; an amino radical; a C1-C20 alkyl or aryl amido radical; a C1-C20 alkyl, alkenyl, aryl, alkylaryl, or arylalkyl radical; or a C1-C20 alkylidene radical; and X is halogen.

The transition metal complex may be represented by one of the formulae below:

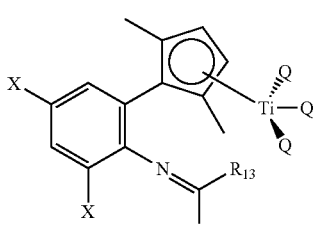

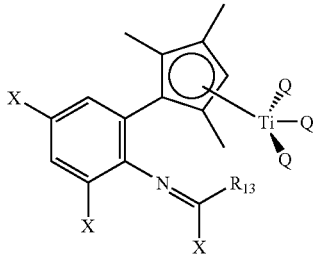

-continued

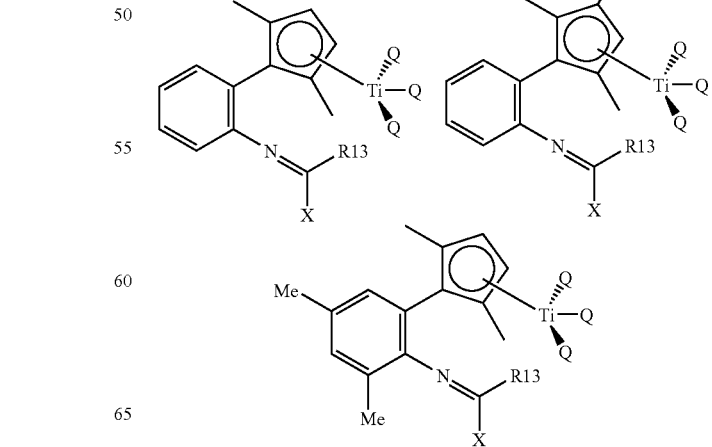

-continued

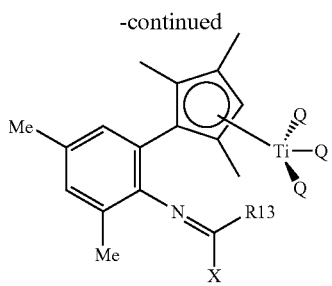

where $R_{13}$ is hydrogen, methyl, a t-butyl or t-butoxy radical, X is halogen, and Q is alkyl, halogen, or amino radical.

According to another aspect of the present invention, there is provided a method of synthesizing a transition metal complex represented by Formula 1, the method including:

synthesizing a compound of Formula 4 by reacting a boronic acid compound of Formula 2 with a 2-bromoaniline compound of Formula 3;

synthesizing a compound of Formula 5 by reacting the compound of Formula 4 with $R^1Li$ and then adding an acid thereto;

synthesizing a compound of Formula 6 by reacting the compound of Formula 5 with $R_5X$ where X is halogen; and synthesizing a complex of Formula 1 by reacting the compound of Formula 6 and a compound of Formula 7 and then adding $(CH_3)_nSiX_{4-n}$ where X is halogen and n is 0, 1, 2, or 3 thereto:

(1)

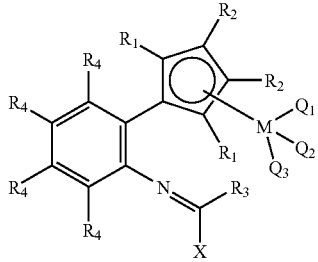

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;

$R_4$ is a hydrogen atom; a halogen radical; or a C1-C20 alkyl or aryl radical, wherein two $R_4$ may be connected to form a fused ring structure;

$R_3$ is a hydrogen atom; a C1-C20 alkyl or aryl radical; or a C1-C20 alkoxy or aryloxy radical;

M is a transition metal of Group 4;

$Q_1$, $Q_2$, and $Q_3$ are each independently a halogen radical; an amino radical; a alkyl or aryl amido radical; a C1-C20 alkyl, alkenyl, aryl, alkylaryl, or arylalkyl radical; or a C1-C20 alkylidene radical;

X is halogen;

(2)

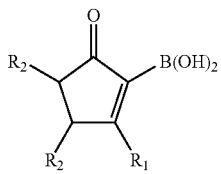

where $R_1$ and $R_2$ are described above;

(3)

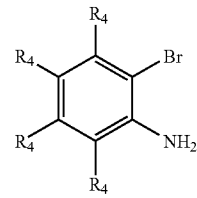

where $R_4$ is described above;

(4)

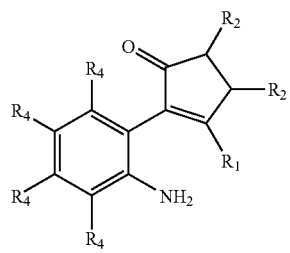

where $R_1$, $R_2$, and $R_4$ are described above;

(5)

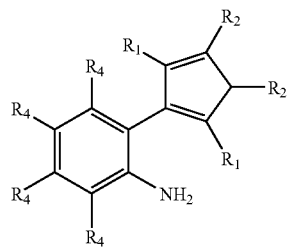

where $R_1$, $R_2$, and $R_4$ are described above;

(6)

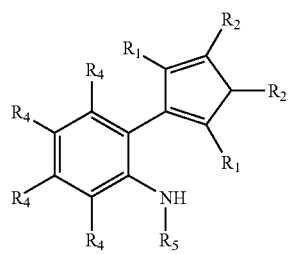

where $R_1$, $R_2$, and $R_4$ are described above, $R_5$ is a C1-C20 alkyl sulfonyl, aryl sulfonyl, or silyl sulfonyl radical; a C1-C20 alkyl carbonyl, aryl carbonyl, or silyl carbonyl radical; a C1-C20 alkyl carboxy, or aryl carboxy radical; or C1-C20 alkyl phosphonyl, or aryl phosphonyl radical; and $$M(N(R_6)_2)_4 \qquad (7)$$

where $R_6$ is a C1-C20 alkyl or aryl radical.

According to another aspect of the present invention, there is provided a method of synthesizing a transition metal complex represented by Formula 1, the method including:

synthesizing a compound of Formula 4 by reacting a boronic acid compound of Formula 2 with a 2-bromoaniline compound of Formula 3;

reacting the compound of Formula 4 with $R_5X$ where X is halogen to obtain a reaction product;

synthesizing a compound of Formula 6 by reacting the reaction product with $R_1Li$ and then adding an acid thereto; and synthesizing a complex of Formula 1 by reacting a compound of Formula 6 with a compound of Formula 7 and then adding $(CH_3)_nSiX_{4-n}$ where X is halogen and n is 0, 1, 2, or 3 thereto;

According to another aspect of the present invention, there is provided a catalyst composition including:

the transition metal complex; and at least one cocatalyst compound selected from the group consisting of compounds represented by Formulae 8 through 10:

—[Al(R$_7$)—O]$_a$—     (8)

where $R_7$ is a halogen radical; a C1-C20 hydrocarbyl radical; or a C1-C20 hydrocarbyl radical substituted with halogen, a is an integer of 2 or greater;

D(R$_7$)$_3$     (9)

where D is aluminum or boron, $R_7$ is described above; and

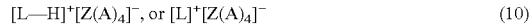

[L—H]$^+$[Z(A)$_4$]$^-$, or [L]$^+$[Z(A)$_4$]$^-$     (10)

where L is a neutral or cationic Lewis acid, H is a hydrogen atom; Z is an element of Group 13; and A is each independently a C6-C20 aryl or alkyl radical at which at least one hydrogen atoms are substituted with halogen or a C1-C20 hydrocarbyl, alkoxy, or penoxy radical.

According to another aspect of the present invention, there is provided a method of preparing a catalyst composition, the method including:

contacting the transition metal complex with the compound of one of Formulae 8 and 9, thereby obtaining a mixture; and adding a compound of Formula 10 to the mixture.

The ratio of the transition metal complex to the compound of Formula 8 or Formula 9 may be in the range of 1:2 through 1:5000, and the ratio of the transition metal complex to the compound of Formula 10 may be in the range of 1:1 through 1:25.

According to another aspect of the present invention, there is provided a method of synthesizing an olefin polymer, including contacting the catalyst composition with a monomer.

The monomer may contain at least one monomer selected from the group consisting of ethylene, propylene, 1-butene, 1-pentene, 4-methyl-1-pentene, 1-hexene, 1-hepthene, 1-octene, 1-decene, 1-undecene, 1-dodecene, 1-tetradecene, 1-hexadecene, and 1-itosen.

According to another aspect of the present invention, there is provided an olefin polymer synthesized using the method of synthesizing an olefin polymer.

The monomer that is used to synthesize the olefin polymer may include: ethylene; and at least one compound selected from the group consisting of propylene, 1-butene, 1-hexene, 4-methyl-1-pentene, and 1-octene.

BRIEF DESCRIPTION OF THE DRAWINGS

The above and other features and advantages of the present invention will become more apparent by describing in detail exemplary embodiments thereof with reference to FIG. 1 illustrating an X-ray structure of [1-(2-t-butylchloroimino)phenyl-2,5-dimethylcyclopentadienyl]titanium trichloride that is a transition metal complex according to an embodiment of the present invention.

DETAILED DESCRIPTION OF THE INVENTION

Figure 1:
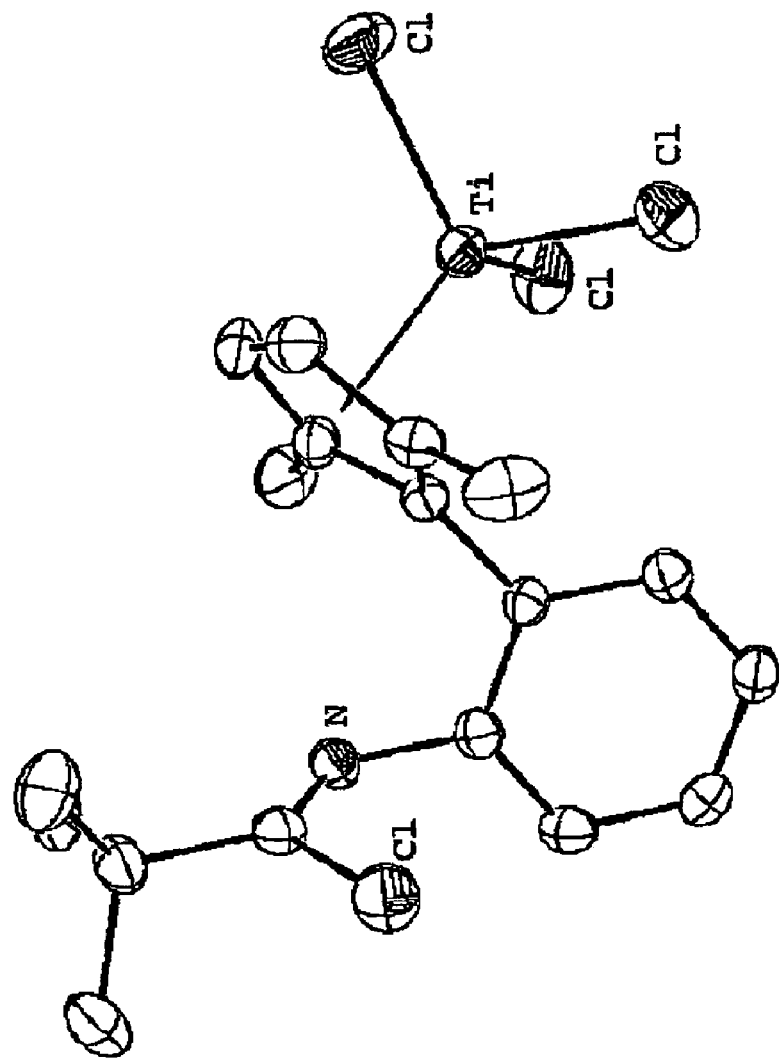

The present invention will now be described more fully with reference to the accompanying drawing.

A transition metal complex according to an embodiment of the present invention has a novel structure in which an imino phenyl group is not bridged to a metal atom and directly connected to a Cp ring, compared to a conventional transition metal complex that contains a single cyclopentadienyl group for preparation of syndiotactic polystyrene (sPS) or to a transition metal compound in which a cyclopentadienyl group is bridged to a metal atom. By using a catalyst composition including the transition metal complex according to an embodiment of the present invention, a polyolefin copolymer having a very low density less than 0.910 g/cc can be obtained.

The transition metal complex according to an embodiment of the present invention may be represented by Formula 1:

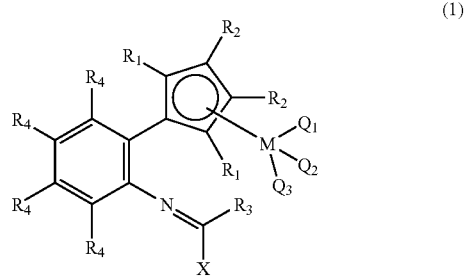

(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring; $R_4$ is each independently a hydrogen atom; a halogen radical; or a C1-C20 alkyl or aryl radical, wherein two $R_4$ may be connected to form a fused ring structure; $R_3$ is hydrogen atom; a C1-C20 alkyl or aryl radical; or a C1-C20 alkoxy or aryloxy radical; M is a transition metal of Group 4; $Q_1$, $Q_2$, and $Q_3$ are each independently a halogen radical; an amino radical; a C1-C20 alkyl or aryl amido radical; a C1-C20 alkyl, alkenyl, aryl, alkylaryl, or arylalkyl radical; or a C1-C20 alkylidene radical; and X is halogen.

The transition metal complex of Formula 1 has a piano-stool shaped structure in which an iminophenyl group is introduced to a cyclopentadienyl ligand and no bridge is formed. The piano-stool shaped transition metal complex is illustrated in FIG. 1. The CpTiCl$_3$ has a similar structure to a catalyst for preparation of syndiotactic polystyrene (sPS), but a compound in which an imino phenyl functional group is directly introduced to at a specific site of a Cp ring and a method of preparing the compound has not been developed.

In addition, various substituents can be introduced to a cyclopentadienyl ring, nitrogen, and a phenylene ring so that electronic and steric environments in the vicinity of metal can be easily controlled to obtain desired structure and properties of a polymer which will be formed.

The transition metal complex of Formula 1 may be represented by one of the structures below, but is not limited thereto.

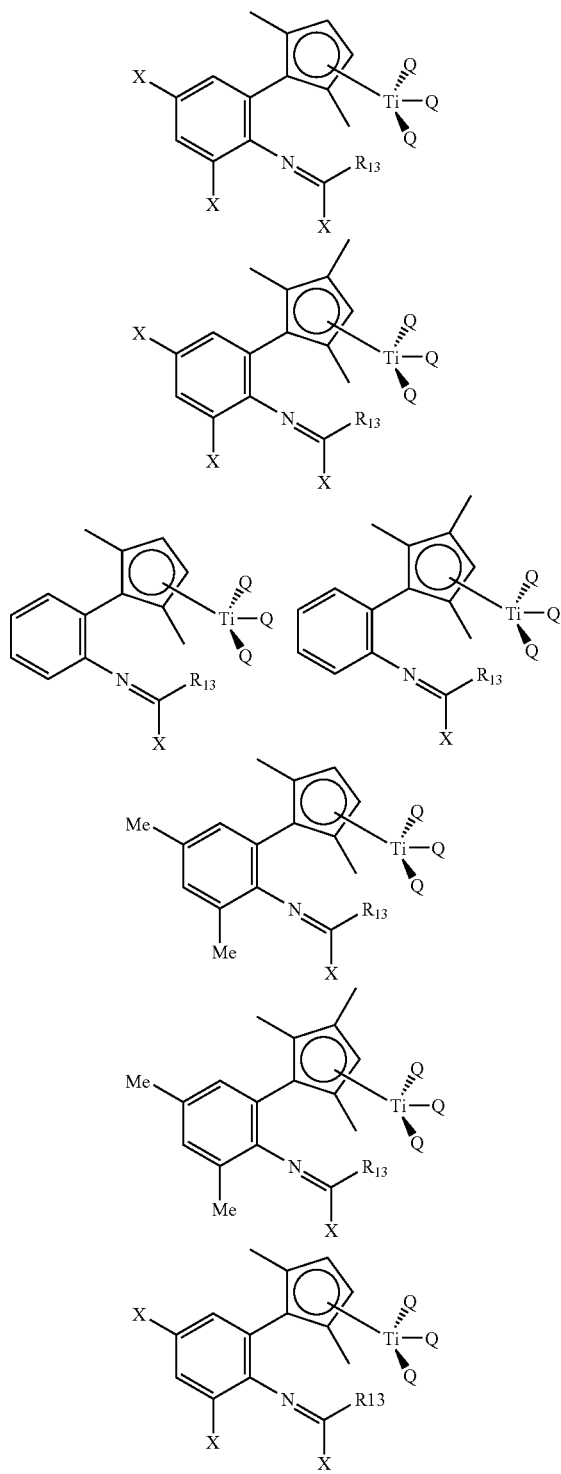

-continued

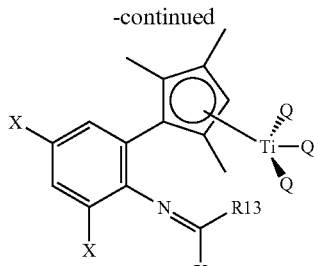

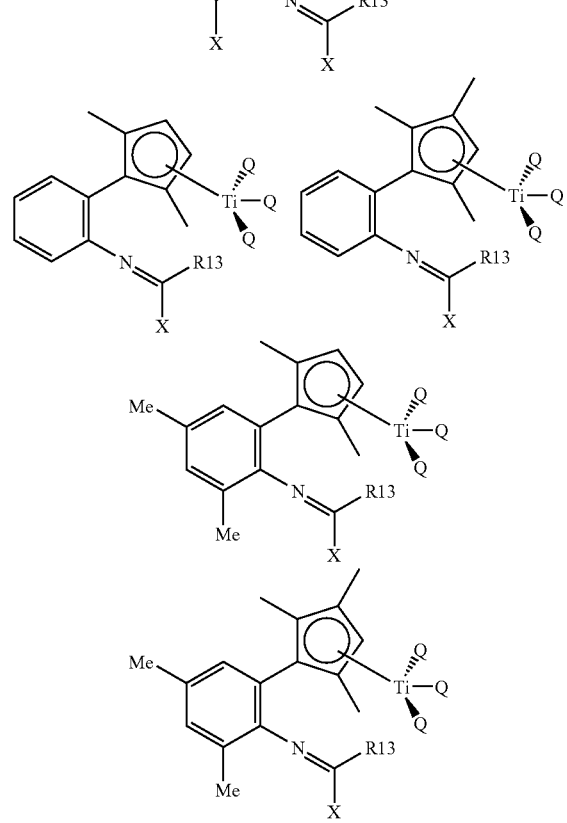

where $R_{13}$ is hydrogen, methyl, a t-butyl or t-butoxy radical, X is halogen, and Q is alkyl, halogen, or amino radical.

A method of preparing a Group 4 transition metal complex of formula 1 according to an embodiment of the present invention will now be described in detail. In order to obtain a novel monocyclopentadienyl ligand in which phenylene of Formula 4 acts as a bridge, a substituted boronic acid is reacted with an aniline compound in the presence of Pd metal catalyst by carbon-carbon coupling, which is Suzuki Reaction. The Suzuki Reaction is well known in the organic chemistry to form a C—C bond, and can be used to synthesize a monocyclopentadienyl ligand of Formula 4 in which various substituents are introduced to cyclopentadienyl, nitrogen, and a phenylene bridge. Ultimately, the transition metal complex of Formula 1 in which electronic and steric hindrance is controlled in the vicinity of metal can be synthesized.

Particularly, the method of synthesizing a transition metal complex represented by Formula 1 includes: a) synthesizing a compound of Formula 4 by reacting a boronic acid compound of Formula 2 with a 2-bromoaniline compound of Formula 3; b) synthesizing a compound of Formula 5 by reacting the compound of Formula 4 with $R_1Li$ and then adding an acid thereto; c) synthesizing a compound of Formula 6 by reacting the compound of Formula 5 with $R_5X$ where X is halogen; and d) synthesizing a complex of Formula 1 by reacting the compound of Formula 6 and a compound of Formula 7 and then adding $(CH_3)_nSiX_{4-n}$ where X is halogen and n is 0, 1, 2, or 3 thereto:

(2)

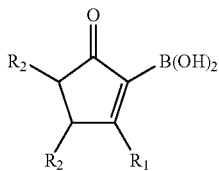

where $R_1$ and $R_2$ are described above;

(3)

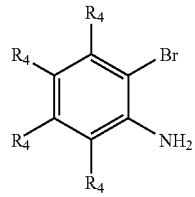

where $R_4$ is described above;

(4)

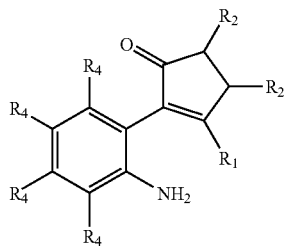

where $R_1$, $R_2$, and $R_4$ are described above;

(5)

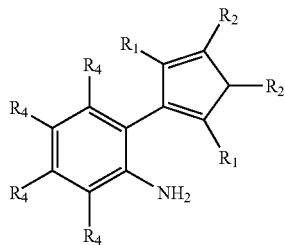

where $R_1$, $R_2$, and $R_4$ are described above;

(6)

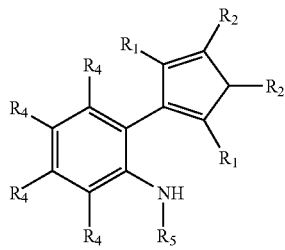

where $R_1$, $R_2$, and $R_4$ are described above, $R_5$ is a C1-C20 alkyl sulfonyl, aryl sulfonyl, or silyl sulfonyl radical; a C1-C20 alkyl carbonyl, aryl carbonyl, or silyl carbonyl radical; a C1-C20 alkyl carboxy, or aryl carboxy radical; or C1-C20 alkyl phosphonyl, or aryl phosphonyl radical; and $$M(N(R_6)_2)_4 \quad (7)$$

where $R_6$ is a C1-C20 alkyl or aryl radical.

The method of preparing the complex of Formula 1 may be represented by:

Reaction Scheme 1

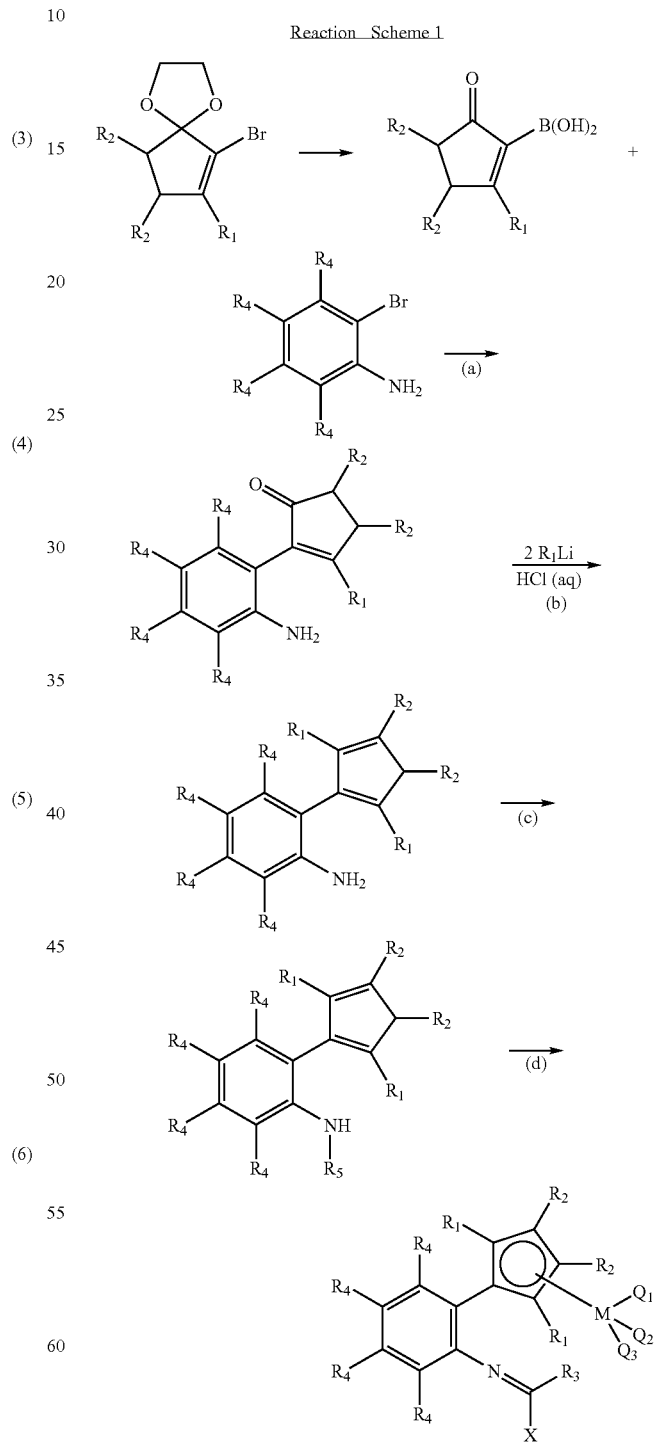

In operation (a), the boronic acid compound of Formula 2 can be obtained by reacting an unsaturated keton compound with a boron triester compound in a solvent of THF or ether and then adding an acid thereto, and the boronic acid compound of Formula 2 is reacted with a boromoaniline compound in the presence of a palladium catalyst via Suzuki Coupling reaction to form an amine-based compound of Formula 4. The palladium catalyst used can be a phosphine compound of Formula 11 which is well known. For example, the palladium catalyst is tetrakis(triphenylphosphine)palladium.

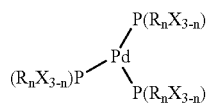
(11)

where R is alkyl or aryl; and X is a halogen atom.

In operation (b), a compound of Formula 4 is reacted with an $R_1Li$ compound at low temperature and then an acid treatment is performed, thereby obtaining a compound of Formula 5. In order to increase the reactivity of the $R_1Li$ compound, the $R_1Li$ compound can be used together with a metal Lewis acid such as $CeCl_3$. In the $R_1Li$ compound, $R_1$ is selected from a C1-C20 alkyl or aryl; a C1-C20 alkenyl, alkylaryl, or arylalkyl; and a metalloid radical of Group 14 metal substituted with hydrocarbyl, preferably is a C1-C10 alkyl or aryl radical, and more preferably is selected from methyl, t-butyl, phenyl, benzyl, and (trimethyl)silylmethyl.

In operation (c), a compound of Formula 5 is reacted with $R_5$—X where X is a halogen atom in the presence of an amine-based base, such as pylidine or triethylamin so that an acid such as H—X is removed and a compound of Formula 6 can be obtained. In the $R_5$—X, $R_5$ is selected from a C1-C20 alkyl carbonyl or aryl carbonyl radical, and a C1-C20 alkyl carboxyl or aryl carboxyl radical, and is preferably selected from methylcarbonyl, t-butylcarbonyl, methylcarboxyl, and t-butylcarboxyl.

In operation (d), the monocyclopentadienyl ligand of Formula 6 prepared above is reacted with a Group 4 metal amino compound of Formula 7, and then $(CH_3)_nSiX_{4-n}$ where X is halogen and n is 0, 1, 2, or 3 is added thereto, thereby obtaining the Group 4 transition metal complex of Formula 1 having a piano-stool shape. The Group 4 metal amino compound is selected from tetrakis(dimethylamino)titanium, tetrakis(diethylamino)titanium, tetrakis(dimethylamino)zirconium, tetrakis(diethylamino)zirconium, tetrakis(dimethylamino)hafnium, and tetrakis(diethylamino)hafnium, and preferably selected from tetrakis(dimethylamino)titanium, tetrakis(dimethylamino)zirconium, and tetrakis(dimethylamino)hafnium. The reaction temperature of the monocyclopentadienyl ligand with the Group 4 metal amino compound may be in the range of 30° C.-150° C., preferably 50° C.-120° C., and more preferably 50° C.-100° C. The reaction time of the monocyclopentadienyl ligand with the Group 4 metal amino compound may be in the range of 6-168 hours, preferably 10-72 hours, and more preferably 12-48 hours. When the reaction temperature is less than 30° C., the ligand is insufficiently reacted with the metal amino compound and thus the yield and purity of the reaction product decrease. When the reaction temperature is higher than 150° C., the reaction product is thermally unstable and thus the yield and purity of the reaction product decreases. When the reaction time is shorter than 6 hours, the ligand is insufficiently reacted with the metal amino compound, whereas when the reaction time is longer than 168 hours, the obtained products may be changed into a different metal compound. The obtained metal compound may have a structure (A) below in which both cyclopentadienyl and nitrogen are bonded to metal. In operation (d), the silane compound may be selected from chlorotrimethylsilane, dichlorodimethylsilane, trichloromethylsilane, and tetrachlorosilane. The mol ratio of the Group 4 metal compound that will react to the silane compound may be in the range of 1:1 to 1:5, and preferably 1:2 to 1:4. When the mol ratio of the Group 4 metal compound to the silane compound is less than 1:1, the chloride substitution occurs insufficiently and thus the yield and purity of the product decrease. On the other hand, when the mol ratio of the Group 4 metal compound to the silane compound is greater than 1:5, the obtained product can be changed into a different metal compound due to excess silane compound. In this case, however, excess silane compound may not affect significantly.

As shown in Reaction Scheme 2, a metal-nitrogen bond in Structure A is broken by the silane compound, and thus the metal compound obtained having Structure B the same as Formula 1 can be obtained. That is, according to an embodiment of the present invention, a monocyclopentadienyl Group 4 metal compound having a piano-stool shape in which an amino functional group is located at a specific site can be easily prepared:

Reation Scheme 2

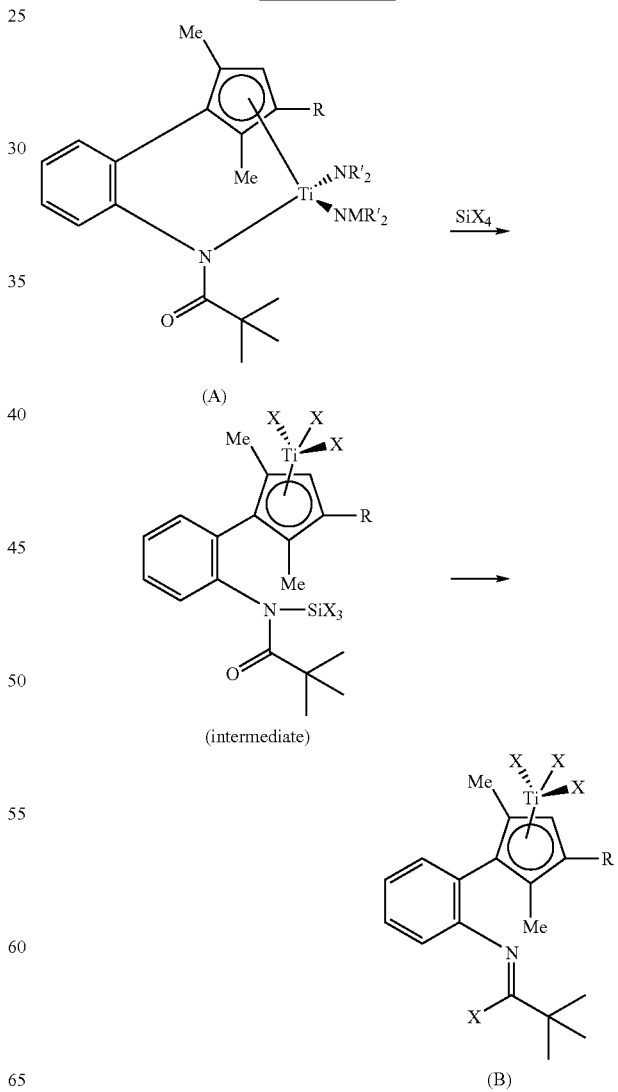

A method of preparing a Group 4 transition metal complex of formula 1 according to another embodiment of the present invention will now be described in detail. The method includes: a) synthesizing a compound of Formula 4 by reacting a boronic acid compound of Formula 2 with a 2-bromoaniline compound of Formula 3; b') reacting the compound of Formula 4 with $R_5X$ where X is halogen to obtain a reaction product; c') synthesizing a compound of Formula 6 by reacting the reaction product with $R_1Li$ and then adding an acid thereto; and d) synthesizing a complex of Formula 1 by reacting a compound of Formula 6 with a compound of Formula 7 and then adding $(CH_3)_nSiX_{4-n}$ where X is halogen and n is 0, 1, 2, or 3 thereto. The present method is the same as the previous method, except that operation b and operation c of the previous method correspond to operation c' and operation b' of the present method, respectively. Respective operations of the present method is the same as in the previous method.

A catalyst composition according to an embodiment of the present invention including: the transition metal complex of the formula 1; and at least one cocatalyst compound selected from compounds represented by Formulae 8 through 10, and the catalyst composition can be used for homopolymerization or copolymerization of olefin:

$$—[Al(R_7)—O]_a— \tag{8}$$

where $R_7$ is each independently a halogen radical; a C1-C20 hydrocarbyl radical; or a C1-C20 hydrocarbyl radical substituted with halogen, a is an integer of 2 or greater;

$$D(R_7)_3 \tag{9}$$

where D is aluminum or boron, $R_7$ is described above; and

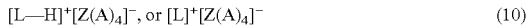
$$[L—H]^+[Z(A)_4]^-, \text{ or } [L]^+[Z(A)_4]^- \tag{10}$$

where L is a neutral or cationic Lewis acid, H is a hydrogen atom; Z is an element of Group 13; and A is each independently a C6-C20 aryl or alkyl radical in which at least one hydrogen atom is substituted with halogen or a C1-C20 hydrocarbyl, alkoxy, or penoxy radical.

A method of preparing the catalyst composition according to an embodiment of the present invention include contacting the transition metal complex of formula 1 with the compound of Formula 8 or Formula 9 to obtain a mixture, and adding a compound of Formula 10 to the mixture. A method of preparing the catalyst composition according to another embodiment of the present invention includes contacting the transition metal complex of Formula 1 with the compound of Formula 8.

In the former method of preparing a catalyst composition, the mole ratio of the transition metal complex to the compound of Formula 8 or Formula 9 may be in the range of 1:2 to 1:5,000, preferably 1:10 to 1:1,000, and preferably 1:20 to 1:500, and the ratio of the transition metal complex to the compound of Formula 10 may be in the range of 1:1 to 1:25, preferably 1:1 to 1:10, and most preferably 1:2 to 1:5. When the ratio of the transition metal complex to the compound of Formula 8 or Formula 9 is less than 1:2, the amount of the alkylating agent is so small that the metal compound is insufficiently alkylated. On the other hand, the ratio of the transition metal complex to the compound of Formula 8 or Formula 9 is greater than 1:5,000, the metal compound is alkylated, but excess alkylating agent can react with the activator of Formula 10 so that the alkylated metal compound is less activated. When the ratio of the transition metal complex to the compound of Formula 10 is less than 1:1, the amount of the activator is relatively small so that the metal compound is less activated. On the other hand, when the ratio of the transition metal complex to the compound of Formula 10 is greater than 1:25, the metal compound may be completely activated but excess activator remains, that is, the preparation process for the catalyst composition is expensive, and the obtained polymer purity is poor.

In the latter method of preparing the catalyst composition, the mole ratio of the transition metal complex to the compound of Formula 8 may be in the range of 1:10 to 1:10,000, preferably 1:100 to 1:5,000, and most preferably 1:500 to 1:2,000. When the mole ratio of the transition metal complex to the compound of Formula 8 is less than 1:10, the amount of the compound of Formula 8 is relatively small so that the transition metal complex is less activated and the obtained catalyst composition has low activity. On the other hand, when the mole ratio of the transition metal complex to the compound of Formula 8 is greater than 1:10,000, the metal compound is completely activated but excess activator remains, that is, the preparation process for the catalyst composition is expensive, and the obtained polymer purity is poor.

The reaction solvent used to preparing the activated catalyst composition can be a hydrocarbon based solvent, such as pentane, hexane, and heptane, or an aromatic solvent, such as benzene and toluene. Also, the transition metal complex of Formula 1 and the cocatalysts can be supported by silica or alumina for use.

Examples of the compound of Formula 8 may include methylaluminoxane, ethylaluminoxane, isobutylaluminoxane, butylaluminoxane etc. For example the compound of Formula 8 is methylaluminoxane.

Examples of the alkyl metal compound of Formula 9 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummetoxide, dimethylaluminumetoxide, trimethylboron, triethylboron, triisobutylboron, tripropylboron, tributylboron etc. For example, the alkyl metal compound of Formula 9 is trimethylaluminum, triethylaluminum, or triisobutylaluminum.

Examples of the compound of Formula 10 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoro methylphenyl)boron, trimethylammoniumtetra(p-trifluoromethylphenyl)boron, tributylammoniumtetrapentafluorophenylboron, N,N-diethylanilinium tetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniu mtetra(p-tolyl)boron,tripropylammoniu mtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron etc.

A method of preparing a homopolymer or copolymer of polyolefin according to an embodiment of the present invention includes contacting a catalyst composition that contains the complex of Formula 1 and at least one compound selected from compounds of Formulae 8 through 10 with at least one olefin monomer.

A polymerization process using the catalyst composition may be a solution process, but when the catalyst composition is used together with an inorganic support, such as silica, the polymerization process can also be a slurry or gas process.

The catalyst composition can be melted or diluted in a solvent suitable for olefin polymerization, before being used. The solvent can be a C5-C12 aliphatic hydrocarbon solvent, such as pentane, hexane, heptane, nonane, decane, or isomers of these; an aromatic hydrocarbon, such as toluene or benzene; or a hydrocarbon solvent that is substituted with a chloride atom, such as dichloromethane or chlorobenzene. The solvent used therein may be treated with a small amount of alkylaluminum to remove water or air, which acts as a catalyst poison, and when needed, the more cocatalysts such as alkylaluminium can be used for the same purpose.

Examples of an olefin based monomer that can be polymerized using the metal complexes and the cocatalysts may include ethylene, alpha-olefin, cyclic olefin etc. In addition, a diene or triene olefin-based monomer having at least two double bonds can be polymerized. In particular, the olefin-based monomer can be ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbonadiene, ethyllidenenorbonene, phenylnorbonene, vinyinorbonene, dicyclopentadiene, 1,4-butadiene, 1,5-pentadiene, 1,6-hexadiene, styrene, alpha-methylstyrene, divinylbenzene, or 3-chloromethylstyrene. In addition, at least two different monomers of these can be copolymerized. The catalyst composition according to an embodiment of the present invention is used to copolymerize ethylene and 1-octene having large steric hindrance to thereby obtain a copolymer having high molecular weight but having a very low density less than 0.910 g/cc.

A monomer of the copolymer may include ethylene and at least one compound selected from propylene, 1-butene, 1-hexene, and 4-methyl-1-pentene, and 1-octene.

The present invention will be described in further detail with reference to the following examples. These examples are for illustrative purposes only and are not intended to limit the scope of the present invention.

Synthesis of Ligand and Transition Metal Complex

Organic reagents and solvents were obtained from Aldrich Co., Inc. and Merck Co., Inc. and purified using a standard method. Each process for the synthesis was performed being isolated from air and moisture to improve reproducibility of experiments. The structure of compounds was identified using a 400 MHz nuclear magnetic resonance (NMR) and an X-ray spectrometer.

EXAMPLE 1

2-dihydroxyboryl-3-methyl-2-cyclopentene-1-one 44.80 g (204.49 mmol) of 2-bromo-3-methyl-2-cyclopentene-1-one ethylene ketal compound were mixed with 240 mL of THF, and then 82 mL(204.49 mmol) of n-BuLi (2.5M in hexane) was added thereto at −78° C. The resultant mixture was mixed at −78° C. for one hour. Then, 42.31 g (224.95 mmol) of boron triisopropyl ester was added to the reaction product and then mixed at −60° C. or less for one hour. The resultant mixture was further reacted at −50° C. for 30 minutes, and then 110 mL of 2 N HCl was added thereto and mixed for 10 minutes. Subsequently, the reaction product was loaded to a separating funnel, 200 mL of ethanol (E.A) was added thereto, and then an organic layer was extracted therefore. 55 mL of ethanol (E.A) was used twice to extract the organic layer. These collected organic layer were dried over $MgSO_4$ to remove water therein and filtered using a glass filter. The solvent contained in the dried product was removed using a rotary vacuum evaporator to obtain a solid product. The solid product was melted using 300 mL of E.A and then twice recrystallized at −30° C. The remaining organic layer was column chromatographed (hexane:E.A=1:1) to remove by-products, and then recrystallized (24.30 g, 85%)

$^1$H NMR ($CDCl_3$): =6.75(s, 2H, OH), 2.69-2.67 (m, 2H, $CH_2$), 2.51-2.49 (m, 2H, $CH_2$), 2.45 (s, 3H, $CH_3$); $^{13}C\{^1H\}$ NMR ($CDCl_3$): =217.35, 193.42, 35.73, 35.12, 20.42

EXAMPLE 2

2-dihydroxyboryl-3,4-dimethyl-2-cyclopentene-1-one 2-dihydroxyboryl-3,4-dimethyl-2-cyclopentene-1-one was obtained in the same manner as in Example 1 using 2-bromo-3,4-dimethyl-2-cyclopentene-1-one ethylene ketal compound (86%).

$^1$H NMR ($CDCl_3$): δ 1.24 (d, J=3.6 Hz, 3H, $CH_3$), 2.09 (dd, J=19, 2.0 Hz, 1H, $CH_2$), 2.39 (s, 3H, $CH_3$), 2.72 (dd, J=19, 6.8 Hz, 1H, $CH_2$), 2.84-2.86 (m, 1H, CH), 7.29 (s, 2H, OH) ppm. $^{13}C\{^1H\}$ NMR ($CDCl_3$): δ 18.01, 18.90, 40.76, 44.22, 197.08, 216.12 ppm.

EXAMPLE 3

2-(2-aminophenyl)-3-methyl-2-cyclopentene-1-one 4.00 g (28.584 mmol) of 2-dihydroxyboryl-3-methyl-2-cyclopentene-1-on compound, 0.30 g (0.260 mmol) of tetrakis(triphenylphosphine)palladium, 4.13 g (38.978 mmol) of sodium carbonate were loaded to 250 mL schlenk flask, and then 80 mL of degassing DME and 27 mL of $H_2O$ that had been purged with $N_2$ were added thereto using a syringe. 3 mL or 4.47 g (25.985 mmol) of 2-bromoaniline was added to the flask using a syringe and reacted at 90° C. for 12 hours.

Subsequently, the reaction product, 200 mL of ethylacetate, and 100 mL of $H_2O$ were added to a separating funnel. Then, the organic layer was extracted. Thereafter, 100 mL of ethylacetate was added to the aqueous layer to extract organic layer again. The organic layer were dried over MgSO₄ to remove water therein and then a rotary vacuum evaporator was used to remove the remaining solvent. Then, the resultant organic layer was column chromatographed (hexane:E.A=1: 1) (3.55 g, 73%).

$^1$H NMR (CDCl$_3$): =7.12 (td, J=7.6 Hz, 1H, Ph), 6.89 (dd, J=7.6 Hz, 1H, Ph), 6.77 (td, J=7.6 Hz, 1H, Ph), 6.72 (dd, J=7.6 Hz, 1H, Ph), 3.72 (br s, 2H, NH$_2$), 2.71 ?? 2.68 (m, 2H, CH$_2$$^{Cp}$), 2.56 ?? 2.54 (m, 2H, CH$_2$$^{Cp}$), 2.08 (s, 3H, CH$_3$); $^{13}$C{$^1$H} NMR (CDCl$_3$): =207.84, 174.84, 144.60, 139.42, 130.44, 128.73, 118.13, 117.84, 116.30, 34.74, 32.13, 18.56

EXAMPLE 4

2-(2-amino)phenyl-3,4-dimethyl-2-cyclopentene-1-one

Yellow oil was obtained in the same manner as in Example 3, except that 4.000 g (25.984 mmol) of 2-dihydroxyboryl-3, 4-dimethyl-2-cyclopentene-1-one, 3.443 g (32.497 mmol) of sodium carbonate, 0.751 g (0.650 mmol) of tetrakis(triphenylphosphine)palladium, and 3.725 g (21.653 mmol) of 2-bromoaniline were used (2.872 g, 66%).

$^1$H NMR (CDCl$_3$): δ 1.32(d, J=3.6 Hz, 3H, CH$_3$), 2.07 (s, 3H, CH$_3$), 2.19 (dd, J=18.4, 1.6 Hz, 1H, CH$_2$—H), 2.83 (dd, J=18.4, 6.4 Hz, 1H, CH$_2$—H), 2.86 (qd, J=6.4, 1.6 Hz, 1H, CH—H), 3.72 (br s, 2H, NH$_2$), 6.77 (dd, J=7.6, 1.6 Hz, 1H, Ph), 6.81 (td, J=7.6, 1.6 Hz, 1H, Ph), 6.91 (dd, J=7.6, 1.6 Hz, 1H, Ph), 7.15 (td, J=7.6, 1.6 Hz, 1H, Ph) ppm. $^{13}$C{$^1$H} NMR (CDCl$_3$): δ 16.39, 19.39, 37.97, 43.51, 116.60, 117.01, 118.16, 118.55, 128.97, 130.67, 144.45, 178.93, 207.02 ppm.

EXAMPLE 5

2-(2-amino-3,5-dimethyl)phenyl-3,4-dimethyl-2-cyclopentene-1-one

White solid was obtained in the same manner as in Example 3, except that 3.459 g (22.465 mmol) of 2-dihydroxyboryl-3,4-dimethyl-2-cyclopentene-1-one, 2.976 g (28.076 mmol) of sodium carbonate, 0.649 g (0.562 mmol) of tetrakis(triphenylphosphine)palladium, and 3.745 g (18.718 mmol) of 2-bromo-4,6-dimethylaniline were used (3.161 g, 74%).

$^1$H NMR (CDCl$_3$): δ 1.32(d, J=3.6 Hz, 3H, CH$_3$), 2.04 (s, 3H, CH$_3$), 2.18 (s, 3H, CH$_3$), 2.20 (s, 1H, CH$_2$—H), 2.24 (s, 3H, CH$_3$), 2.82 (dd, J=18.4, 6.4 Hz, 1H, CH$_2$—H), 2.94 (qd, J=6.4, 1.6 Hz, 1H, CH—H), 3.48 (br s, 2H, NH$_2$), 6.60 (s, 1H, Ph), 6.88 (s, 1H, Ph) ppm. $^{13}$C{$^1$H} NMR (CDCl$_3$): δ 16.19, 17.76, 19.32, 20.37, 37.67, 43.45, 117.42, 122.79, 126.74, 128.44, 130.88, 140.02, 178.58, 106.85 ppm.

EXAMPLE 6

2-(2-amino-3,5-difluoro)phenyl-3,4-dimethyl-2-cyclopentene-1-one

White solid was obtained in the same manner as in Example 3, except that 2.000 g (12.990 mmol) of 2-dihydroxyboryl-3,4-dimethyl-2-cyclopentene-1-one, 1.967 g (18.557 mmol) of sodium carbonate, 0.429 g (0.371 mmol) of tetrakis(triphenylphosphine)palladium, and 2.436 g (12.371 mmol) of 2-bromo-4,6-difluoroaniline were used (1.938 g, 76%).

$^1$H NMR (CDCl$_3$): δ 1.29(d, J=3.6 Hz, 3H, CH$_3$), 2.04 (s, 3H, CH$_3$), 2.15 (dd, J=18.8, 2.0 Hz, 1H, CH$_2$—H), 2.79 (dd, J=18.8, 14.4 Hz, 1H, CH$_2$—H), 2.93 (q, J=6.4 Hz, 1H, CH—H), 3.65 (br s, 2H, NH$_2$), 6.54 (d, J$_{H-F}$=8.8 Hz, 1H, Ph), 6.78 (t, J$_{H-F}$=8.8 Hz, 1H, Ph) ppm.

EXAMPLE 7

2-(2,5-dimethylcyclopenta-1,4-dienyl)phenylamine 1.973 g (1.581 mmol) of CeCl$_3$ and 10 mL of THF were loaded to a 50 mL flask, and then 5.007 mL (8.011 mmol) of MeLi (1.6 M in diethyl ether) was added thereto at −78° C. and mixed, thereby obtaining a yellow solution. After one hour, 0.600 g (3.204 mmol) of 2-(2-amino)phenyl-3-methyl-2-cyclopentene-1-one melted in 15 mL THF was added to the flask using a syringe and mixed at −78° C. for 2 hours. 10 mL of distilled water was added to the flask and THF therein was removed using a rotary vacuum evaporator. 10 mL of E.A and 5 mL of 2 N HCl were added to the resultant reaction product in which THF had been removed, and then strongly stirred for 3 minutes. The organic phase was collected. Then, 5 mL of E.A was twice added to the aqueous layer to obtain organic compound again. The obtained organic layer was neutralized using 5 mL of NaHCO$_3$. Subsequently, the extracted organic layer was dried over MgSO$_4$ to remove water therein. The dried product was filtered with glass filter to remove CeCl$_3$ and MgSO$_4$, subjected to the solvent removal using a rotary vacuum evaporator, and then column chromatographed (hexane:E.A=5:1). As a result, pure white solid was obtained (0.312 g, 53%).

$^1$H NMR (CDCl$_3$): δ 1.82(d, J=1.6 Hz, 3H, Cp-CH$_3$), 1.92 (s, 3H, Cp-CH$_3$), 3.01 (q, J=1.6 Hz, 2H, Cp-CH$_2$), 3.80 (br s, 2H, NH$_2$), 5.99 (q, J=1.6 Hz, 1H, Cp-CH), 6.78 (dd, J=7.6, 1.6 Hz, 1H, Ph), 6.79 (td, J=7.6, 1.6 Hz, 1H, Ph), 6.97 (dd, J=7.6, 1.6 Hz, 1H, Ph), 7.14 (td, J=7.6, 1.6 Hz, 1H, Ph) ppm. $^{13}$C{$^1$H} NMR (CDCl$_3$): δ 14.68, 14.77, 44.39, 114.70, 117.79, 122.17, 124.26, 127.86, 130.19, 139.18, 141.38, 143.63, 144.24 ppm.

EXAMPLE 8

2-(2,5-dimethylcyclopenta-1,4-dienyl)-4,6-dimethylphenylamine

White solid was prepared in the same manner as in Example 7, except that 9.209 g (37.391 mmol) of anhydrous CeCl$_3$, 23.360 mL (37.391 mmol) of MeLi (1.6 M in diethyl ether), and 3.500 g (16.257 mmol) of 2-(2-amino-3,5-dimethyl)phenyl-3-methyl-2-cyclopentene-1-one were used (2.43 g, 70%).

$^1$H NMR (CDCl$_3$): δ 1.83(d, J=1.6 Hz, 3H, Cp-CH$_3$), 1.93 (s, 3H, Cp-CH$_3$), 2.22 (s, 3H, Ph-CH$_3$), 2.28 (s, 3H, Ph-CH$_3$), 3.02 (q, J=1.6 Hz, 2H, Cp-CH$_2$), 3.50 (br s, 2H, NH$_2$), 5.99 (q, J=1.6 Hz, 1H, Cp-CH), 6.68 (s, 1H, Ph), 6.88 (s, 1H, Ph) ppm. $^{13}$C{$^1$H} NMR (CDCl$_3$): δ 14.72, 14.80, 17.94, 20.58, 44.34, 121.88, 122.03, 124.17, 126.33, 128.22, 129.76, 139.65, 139.89, 141.03, 143.75 ppm.

EXAMPLE 9

2-(2,3,5-trimethylcyclopenta-1,4-dienyl)phenylamine

Brown solid was prepared in the same manner as in Example 7, except that 9.598 g (38.973 mmol) of anhydrous CeCl$_3$, 24.358 mL (38.973 mmol) of MeLi (1.6 M in diethyl ether), and 2.615 g (12.991 mmol) of 2-(2-amino)phenyl-3, 4-dimethyl-2-cyclopentene-1-one were used (2.307 g, 89%).

$^1$H NMR (CDCl$_3$): δ 1.56(s, 3H, Cp-CH$_3$), 1.75 (s, 3H, Cp-CH$_3$), 1.85 (s, 3H, Cp-CH$_3$), 2.82 (s, 2H, Cp-CH$_2$), 3.55 (br s, 2H, NH$_2$), 6.62 (dd, J=7.6, 1.6 Hz, 1H, Ph), 6.65 (td, J=7.6, 1.6 Hz, 1H, Ph), 6.82 (dd, J=7.6, 1.6 Hz, 1H, Ph), 6.99 (td, J=7.6, 1.6 Hz, 1H, Ph) ppm. $^{13}$C{$^1$H} NMR (CDCl$_3$): δ 11.67, 13.63, 14.35, 48.80, 114.67, 117.76, 122.79, 127.69, 130.13, 133.14, 135.54, 136.73, 139.61, 144.14 ppm.

EXAMPLE 10

2-(2,3,5-trimethylcyclopenta-1,4-dienyl)-4,6-dimethylphenylamine

Yellow solid was prepared in the same manner as in Example 7, except that 9.666 g (39.246 mmol) of anhydrous CeCl$_3$, 24.529 mL (39.246 mmol) MeLi (1.6 M in diethyl ether), and 3.000 g (13.082 mmol) of 2-(2-amino-3,5-dimethyl)phenyl-3,4-dimethyl-2-cyclopentene-1-one were used (2.241 g, 75%).

$^1$H NMR (CDCl$_3$): δ 1.74(s, 3H, Cp-CH$_3$), 1.93 (s, 3H, Cp-CH$_3$), 2.04 (s, 3H, Cp-CH$_3$), 2.26 (s, 3H, Ph-CH$_3$), 2.33 (s, 3H, Ph-CH$_3$), 3.00 (q, J=2.4 Hz, 2H, Cp-CH$_2$), 3.47 (br s, 2H, NH$_2$), 6.72 (s, 1H, Ph), 6.91 (s, 1H, Ph) ppm. $^{13}$C{$^1$H} NMR (CDCl$_3$): δ 11.72, 13.61, 14.40, 17.88, 20.55, 48.78, 121.78, 122.61, 126.21, 128.20, 129.60, 133.00, 135.66, 136.41, 139.85, 140.07 ppm.

EXAMPLE 11

2-(2,5-dimethylcyclopenta-1,4-dienyl)phenyl(trimethylacetyl)amine 0.130 g (1.29 mmol) of triethylamine and 0.155 g (1.29 mmol) of pivaloyl chloride were added to 0.263 g (1.42 mmol) of 2-(2,5-dimethylcyclopenta-1,4-dienyl)phenylamine dissolved in 10 mL of an MC solvent and then reacted at room temperature for one hour. 5 mL of 2N HCl was added to the reaction solution and then strongly stirred for a few minutes. The organic layer was collected and then neutralized by 5 mL of NaHCO$_3$ saturated aqueous solution. The resultant product was purified through a column chromatography using a solvent of hexane/ethyl acetate (v/v, 10:1), and then dried in vacuum to remove the solvent therein, thereby obtaining white solid (0.355 g, 93%).

$^1$H NMR (CDCl$_3$): 1.18 (s, 9H, C(CH$_3$)$_3$), 1.73 (q, J=1.6 Hz, 3H, Cp-CH$_3$), 1.89 (s, 3H, Cp-CH$_3$), 3.08-3.07 (m, 2H, Cp-CH$_2$), 6.05 (d, J=2.0 Hz, 1H, Cp-CH), 7.07 (dd, 1H, J=7.6, 2.0 Hz, 1H, bz-CH), 7.11 (td, J=7.2, 1.2 Hz, 1H, bz-CH), 7.33 (td, J=8.4, 2.0 Hz, 1H, bz-CH), 7.54 (s, 1H, NH), 8.44 (d, J=8.0 Hz, 1H, bz-CH) ppm; $^{13}$C{$^1$H} NMR (CDCl$_3$): 14.47, 14.64, 27.42, 39.84, 44.59, 119.15, 123.14, 125.27, 128.07, 129.28, 136.02, 138.36, 142.64, 142.76, 175.93 ppm.

EXAMPLE 12

2-(2,5-dimethylcyclopenta-1,4-dienyl)-3,5-dimethylphenyl-(trimethylacetyl)amine 0.717 g (3.36 mmol) of 2-(2,5-dimethylcyclopenta-1,4-dienyl)-3,5-dimethylphenylamine, 0.408 g (4.03 mmol) of triethylamine, and 0.486 g (4.03 mmol) of pivaloyl chloride were used in the same manner as in Example 11. The resultant reaction product was purified using a column chromatography using a toluene/MC (v/v, 1:1) solvent, and then the solvent in the purified product was removed in vacuum, thereby obtaining while solid (0.698 g, 70%).

$^1$H NMR (CDCl$_3$): 1.17 (s, 9H,C(CH$_3$)$_3$), 1.69 (s, 3H, Cp-CH$_3$), 1.85 (s, 3H, Cp-CH$_3$), 2.24 (s, 3H, bz-CH$_3$), 2.34 (s, 3H, bz-CH$_3$), 2.97 (d, J=1.2 Hz, 2H, Cp-CH$_2$), 5.94 (s, 1H, Cp-CH), 6.75 (s, 1H, NH), 6.78 (s, 1H, bz-CH), 7.03 (s, 1H, bz-CH) ppm; $^{13}$C{$^1$H} NMR (CDCl$_3$): 14.54, 14.58, 18.74, 21.08, 27.50, 44.19, 123.88, 127.76, 130.41, 131.19, 132.90, 134.94, 135.59, 140.14, 143.35, 175.85 ppm.

EXAMPLE 13

2-(2,3,5-trimethylcyclopenta-1,4-dienyl)phenyl(trimethylacetyl)amine 0.534 g of (2.68 mmol) of 2-(2,3,5-trimethylcyclopenta-1,4-dienyl)phenylamine, 0.325 g (3.22 mmol) of triethylamine, and 0.388 g (3.22 mmol) of pivaloyl chloride were used in the same manner as in Example 11. The resultant reaction product was purified through a column chromatography using a hexane/ethyl acetate (v/v, 5:1) solvent, and then the solvent in the purified product was removed in vacuum, thereby obtaining white solid (0.674 g, 89%).

$^1$H NMR (CDCl$_3$): 1.17 (s, 9H, C(CH$_3$)$_3$), 1.58 (s, 3H, Cp-CH$_3$), 1.83 (s, 3H, Cp-CH$_3$), 1.98 (s, 3H, Cp-CH$_3$), 3.01 (s, 2H, Cp-CH$_2$), 7.05 (dd, J=7.6, 2.0 Hz, 1H, bz-CH), 7.08 (td, 1H, J=7.6, 1.2 Hz, 1H, bz-CH), 7.30 (td, J=7.6, 1.6 Hz, 1H, bz-CH), 7.60 (s, 1H, NH), 8.44 (d, J=8.4 Hz, 1H, bz-CH) ppm; $^{13}$C{$^1$H} NMR (CDCl$_3$): 11.46, 13.51, 14.17, 27.29, 39.71, 48.87, 118.94, 122.96, 126.21, 127.78, 129.13, 134.27, 134.63, 135.91, 137.91, 137.92, 138.67, 175.75 ppm.

EXAMPLE 14

2-(2,3,5-trimethylcyclopenta-1,4-dienyl)-4,6-dimethylphenyl(trimethylacetyl)amine 2-(2,3,5-trimethylcyclopenta-1,4-dienyl)-4,6-dimethylphenyl(trimethylacetyl)amine was prepared in the same manner as Example 11, except that 0.600 g (2.64 mmol) of 2-(2,3,5-trimethylcyclopenta-1,4-dienyl)-4,6-dimethylphenylamine, 0.321 g (3.17 mmol) of triethylamine, and 0.382 g (3.17 mmol) of pivaloyl chloride were used (0.727 g, 89%).

$^1$H NMR (CDCl$_3$): 1.16 (s, 9H, C(CH$_3$)$_3$), 1.54 (s, 3H, Cp-CH$_3$), 1.80 (s, 3H, Cp-CH$_3$), 1.94 (s, 3H, Cp-CH$_3$), 2.23 (s, 3H, bz-CH$_3$), 2.33 (s, 3H, bz-CH$_3$), 2.91 (brd, J=5.6 Hz, 2H, Cp-CH$_2$), 6.76 (s, 2H, bz-CH), 7.02 (s, 1H, NH) ppm; $^{13}$C{$^1$H} NMR (CDCl$_3$): 11.63, 13.50, 18.79, 21.09, 27.46, 39.13, 48.64, 127.68, 130.28, 131.18, 132.85, 133.22, 134.79, 135.34, 135.47, 135.62, 140.51, 175.77 ppm.

EXAMPLE 15 phenylene(t-butylcarboxamido)(2,5-dimethylcyclopentadienyl)titanium bis(dimethylamine)

50 mL of toluene solvent was added to 0.203 g (0.700 mmol) of 2-(2,5-dimethylcyclopenta-1,4-dienyl)phenyl(trimethylacetyl)amine and 0.156 g (0.700 mmol) of tetrakis(dimethylamino)titanium. The reaction solution was stirred at 80° C. for one day, and then a volatile material was removed therefrom. As a result, red oil was obtained (100% purity of the red oil was identified by $^1$H and $^{13}$C NMR spectrometry).

$^1$H NMR(C$_6$D$_6$): 1.43 (s, 9H,C(CH$_3$)$_3$), 1.94 (s, 6H, Cp-CH$_3$), 2.97 (s, 12H, N—CH$_3$), 5.79 (s, 2H, Cp-CH), 7.01 (td, J=8.4, 1.2 Hz, bz-CH), 7.26 (t,d, J=8.4, 1.6 Hz, 1H, bz-CH), 7.30 (d, J=8.0 Hz, 1H, bz-CH), 7.66 (d, J=8.0 Hz, 1H, bz-CH) ppm; $^{13}$C{$^1$H} NMR (C$_6$D$_6$): 14.73 (Cp-CH$_3$), 29.14

$C(CH_3)_3$), 39.77 ($C(CH_3)_3$), 48.35 ($N-CH_3$), 112.35, 122.81, 125.21, 125.55, 128.54, 131.55, 132.86, 144.65, 168.49 ppm.

EXAMPLE 16

(4,6-dimethyl)phenylene(t-butylcarboxamido)(2,5-dimethylcyclopenta-dienyl)titanium bis(dimethylamine)

7 mL of toluene solvent was added to 0.515 g (1.73 mmol) of 2-(2,5-dimethylcyclopenta-1,4-dienyl)-4,6-dimethylphenyl(trimethylacetyl)amine and 0.388 g (1.73 mmol) of tetrakis(dimethylamino)titanium. The reaction solution was stirred at 80° C. for 5 days, and then a volatile material was removed therefrom. As a result, red oil was obtained (100% purity of the red oil was identified by $^1$H and $^{13}$C NMR spectrometry).

$^1$H NMR($C_6D_6$): 1.43 (s, 9H, $C(CH_3)_3$), 1.97 (s, 6H, Cp-$CH_3$), 2.25 (s, 3H, bz-$CH_3$), 2.62 (s, 3H, bz-$CH_3$), 2.99 (s, 12H, $N-CH_3$), 5.89 (s, 2H, Cp-CH), 6.98 (s, 1H, bz-CH), 7.08 (s, 1H, bz-CH) ppm; $^{13}C\{^1H\}$ NMR ($C_6D_6$): 14.95, 21.15, 21.60, 29.29, 40.30, 48.42, 112.44, 122.68, 124.72, 125.78, 130.92, 131.22, 131.38, 136.98, 140.37, 167.22 ppm.

EXAMPLE 17 phenylene(t-butylcarboxamido)(2,3,5-trimethylcyclopentadienyl)titanium bis(dimethylamine)

6 mL of toluene solvent was added to 0.486 g (1.72 mmol) of 2-(2,3,5-trimethylcyclopenta-1,4-dienyl)phenyl(trimethylacetyl)amine and 0.386 g (1.72 mmol) of tetrakis(dimethylamino)titanium. The reaction solution was stirred at 80° C. for one day, and then a volatile material was removed therefrom. As a result, red oil was obtained (100% purity of the red oil was identified by $^1$H and $^{13}$C NMR spectrometry).

$^1$H NMR($C_6D_6$): 1.45 (s, 9H, $C(CH_3)_3$), 1.88 (s, 3H, Cp-$CH_3$), 1.94 (s, 3H, Cp-$CH_3$), 2.03 (s, 3H, Cp-$CH_3$), 2.81 (s, 6H, $N-CH_3$), 3.14 (s, 3H, $N-CH_3$), 5.86 (s, 1H, Cp-CH), 7.03 (td, J=7.2, 1.2 Hz, 1H, bz-CH), 7.27 (dd, J=7.6, 0.8 Hz, 1H, bz-CH), 7.30 (td, J=7.6, 1.2 Hz, 1H, bz-CH), 7.70 (dd, J=8.0, 0.8 Hz, 1H, bz-CH) ppm; $^{13}C\{^1H\}$ NMR ($C_6D_6$): 12.79, 13.06, 14.13, 29.12, 39.76, 47.12, 49.85, 115.52, 120.22, 121.21, 121.31, 122.78, 125.59, 125.95, 128.48, 131.52, 132.95, 144.69, 168.90 ppm.

EXAMPLE 18

(4,6-dimethyl)phenylene(t-butylcarboxamido)(2,3,5-trimethylcyclopenta-dienyl)titanium bis(dimethylamid)

7 mL of toluene solvent was added to 0.565 g (1.81 mmol) of 2-(2,3,5-trimethylcyclopenta-1,4-dienyl)-4,6-dimethylphenyl(trimethylacetyl)amine and 0.407 g (1.81 mmol) of tetrakis(dimethylamino)titanium. The reaction solution was stirred at 110° C. for four days, and then a volatile material was removed therefrom. As a result, red oil was obtained (about 100% purity of the red oil was identified by $^1$H and $^{13}$C NMR spectrometry).

$^1$H NMR($C_6D_6$): 1.45 (s, 9H, $C(CH_3)_3$), 1.92 (s, 3H, Cp-$CH_3$), 1.99 (s, 3H, Cp-$CH_3$), 2.06 (s, 3H, Cp-$CH_3$), 2.27 (s, 3H, bz-$CH_3$), 2.66 (s, 3H, bz-$CH_3$), 2.83 (s, 6H, $N-CH_3$), 3.17 (s, 6H, $N-CH_3$), 5.89 (s, 1H, Cp-CH), 6.99 (s, 1H, bz-CH), 7.10 (s, 1H, bz-CH) ppm; $^{13}C\{^1H\}$ NMR ($C_6D_6$): 12.85, 13.29, 14.37, 21.19, 21.57, 29.26, 40.28, 47.22, 49.98, 115.62, 119.81, 120.77, 121.33, 125.13, 126.11, 130.89, 131.13, 131.46, 136.96, 140.39, 167.63 ppm.

EXAMPLE 19

[1-(2-t-butylchloroimino)phenyl-2,5-dimethylcyclopentadienyl]titanium trichloride 0.306 g (2.37 mmol) of dichlorodimethylsilane and 8 mL of toluene were added to $C_6H_4$(t-BuCON)(2,5-$Me_2$ Cp)Ti($NMe_2$)$_2$. The reaction solution was stirred at 80° C. for three days, and a volatile material was removed therefrom. The resultant reaction product was washed with 10 mL of a pentane solvent, and then the solvent used was removed in vacuum. As a result, 0.128 g (yield: 42%) of yellow solid was obtained. The X-ray crystalline structure of the yellow solid was illustrated in FIG. 1.

$^1$H NMR($C_6D_6$): 0.915 (s, 9H,$C(CH_3)_3$), 2.20 (s, 6H, Cp-$CH_3$), 6.01 (s, 2H, Cp-CH), 6.50 (dd, J=8.0, 0.8 Hz, 1H, bz-CH), 6.89 (td, J=7.6, 1.2 Hz, 1H, bz-CH), 7.02 (td, J=7.2, 1.6 Hz, 1H, bz-CH), 7.68 (dd, J=8.0, 0.8 Hz, 1H, bz-CH) ppm; $^{13}C\{^1H\}$ NMR ($C_6D_6$): 17.18, 28.12, 42.14, 119.72, 123.59, 125.31, 130.03, 131.92, 139.96, 140.10, 140.74, 147.21, 155.91 ppm.

EXAMPLE 20

[1-(2-t-butylchloroimino)phenyl-2,3,5-trimethylcyclopentadienyl]titanium trichloride 10 mL of dichlorodimethylsilane and 5 mL of toluene was added to $C_6H_4$(t-BuCON)(2,3,5-$Me_3$ Cp)Ti($NMe_2$)$_2$. The reaction solution was stirred at 80° C. for 2 days, and a volatile material was removed therefrom under vacuum. The resultant reaction product was washed with 10 mL of a pentane solvent, and then the solvent used was removed in vacuum, thereby obtaining yellow solid. The X-ray crystalline structure of the yellow solid was illustrated in FIG. 1. (0.150 g, 31%).

$^1$H NMR($C_6D_6$): 0.90 (s, 9H,$C(CH_3)_3$), 1.98 (s, 3H, Cp-$CH_3$), 2.17 (s, 3H, Cp-$CH_3$), 2.2.25 (s, 3H, Cp-$CH_3$), 5.97 (s, 1H, Cp-CH), 6.66 (dd, J=8.0, 1.6 Hz, 1 H, bz-CH), 6.91 (td, J=7.6, 1.2 Hz, 1H, bz-CH), 7.03 (td, J=8.0, 1.6 Hz, 1H, bz-CH), 7.75 (dd, J=8.0, 1.6 Hz, 1H, bz-CH) ppm; $^{13}C\{^1H\}$ NMR ($C_6D_6$): 15.16, 16.33, 17.45, 28.06, 43.82, 119.57, 123.64, 124.68, 125.28, 129.95, 132.17, 137.70, 138.76, 139.14, 141.69, 147.17, 155.64 ppm.

EXAMPLE 21

In-situ synthesis of [1-(2-t-butylchloroimino)phenyl-2,5-dimethylcyclopentadienyl]titanium trichloride 2.06 g (7.65 mmol) of 2-(2,5-dimethylcyclopenta-1,4-dienyl)phenyl(trimethylacetyl)amine, 1.72 g (7.65 mmol) of Ti($NMe_2$)$_4$, and 20 mL of toluene were reacted at 80° C. for one day. The solvent was dried under vacuum to thereby obtain red oil. The obtained bis(dimethylamido)titanium was melted with 20 mL of toluene and then 5.20 g (30.6 mmol) of $SiCl_4$ was added thereto. The resultant solution was reacted at room temperature for four hours and then dried under vacuum to remove a volatile material therefrom. The dried product was washed with 30 mL of pentane to obtain yellow solid (1.77 g, 53%).

$^1$H NMR($C_6D_6$): 0.93 (s, 9H, $C(CH_3)_3$), 2.21 (s, 6H, $CH_3$), 6.03 (s, 2H, Cp-H), 6.65 (d, J=8.4 Hz, 1H, $H^{3\ or\ 6}$), 6.89 (t, J=7.6 Hz, 1H, $H^{4\ or\ 5}$), 7.03 (t, J=8.0 Hz, 1H, $H^{4\ or\ 5}$), 7.67 (d, J=7.6 Hz, 1H, $H^{3\ or\ 6}$) ppm. $^{13}C\{^1H\}$ NMR ($C_6D_6$): 17.19, 28.12, 43.89, 119.74, 123.05, 123.65, 125.28, 130.03, 131.89, 140.15, 140.79, 147.23, 155.97 ppm.

EXAMPLE 22

In-situ synthesis of [1-(2-t-butylchloroimino)phenyl-2,3,5-trimethylcyclopentadienyl]titanium trichloride

[1-(2-t-butylchloroimino)phenyl-2,3,5-trimethylcyclopentadienyl]titanium trichloride was prepared using 2-(2,3,5-Timethylcyclopenta-1,4-dienyl)phenyl(trimethylacetyl)amine in the same manner as in Example 21 (73%).

$^1$H NMR($C_6D_6$): 0.91 (s, 9H, C($CH_3$)$_3$), 2.00 (s, 3H, $CH_3$), 2.17 (s, 3H, $CH_3$), 2.25 (s, 3H, $CH_3$), 5.99 (s, 1H, Cp-H), 6.66 (d, J=8.0 Hz, 1H, $H^{3\ or\ 6}$), 6.91 (tt, J=8.4, 1.2 Hz, 1H, $H^{4\ or\ 5}$), 7.04 (tt, J=8.0, 1.2 Hz, 1H, $H^{4\ or\ 5}$), 7.73 (d, J=8.0 Hz, 10H, $H^{3\ or\ 6}$) ppm. $^{13}$C{$^1$H} NMR($C_6D_6$): 15.19, 16.39, 17.49, 28.08, 43.85, 119.64, 123.63, 124.79, 125.22, 129.96, 132.13, 137.78, 138.85, 139.28, 141.78, 147.20, 155.74 ppm.

EXAMPLE 23

In-situ synthesis of [1-(2-t-butylchloroimino)-3,5-dimethylphenyl-2,5-dimethylcyclopentadienyl]-titanium trichloride

[1-(2-t-butylchloroimino)-3,5-dimethylphenyl-2,5-dimethylcyclopentadienyl]-titanium trichloride was prepared using 2-(2,5-dimethylcyclopenta-1,4-dienyl)-4,6-dimethylphenyl(trimethylacetyl)amine in the same manner as in Example 21 (55%).

$^1$H NMR($C_6D_6$): 0.95 (s, 9H,C($CH_3$)$_3$), 1.95 (s, 3H, $CH_3$), 2.09 (s, 3H, $CH_3$), 2.28 (s, 3H, Ph-$CH_3$), 2.30 (s, 3H, Ph-$CH_3$), 5.90 (d, J=2.8 Hz, 1H, Cp-H), 6.18 (d, J=2.8 Hz, 1H, Cp-H), 6.79 (s, 1H, Ph-H), 7.45 (s, 1H, Ph-H) ppm. $^{13}$C{$^1$H} NMR ($C_6D_6$): 17.05, 17.12, 17.69, 17.75, 21.04, 28.19, 43.81, 121.94, 123.02, 123.11, 124.39, 126.66, 129.86, 129.91, 132.44, 132.51, 134.36, 139.26, 140.70, 141.67, 143.93, 156.11 ppm.

EXAMPLE 24

In-situ synthesis of [1-(2-t-butylchloroimino)-3,5-dimethylphenyl-2,3,5-trimethylcyclopenta-dienyl] titanium trichloride

[1-(2-t-butylchloroimino)-3,5-dimethylphenyl-2,3,5-trimethylcyclopenta-dienyl]titanium trichloride was prepared using 2-(2,3,5-trimethylcyclopenta-1,4-dienyl)-4,6-dimethylphenyl(trimethylacetyl)amine in the same manner as in Example 21(57%).

$^1$H NMR($C_6D_6$): 0.93 (s, 3.9H, C($CH_3$)$_3$), 0.94 (s, 5.1H, C($CH_3$)$_3$), 1.95 (s, 1.3H, $CH_3$), 1.96 (s, 1.7H, $CH_3$), 2.11 (s, 6H, Ph-$CH_3$), 2.25 (s, 1.3H, $CH_3$), 2.27 (s, 1.7H, $CH_3$), 2.32 (s, 1.7H, $CH_3$), 2.34 (s, 1.3H, $CH_3$), 5.85 (s, 0.43H, Cp-H), 6.12 (s, 0.57H, Cp-H), 6.81 (s, 1H, Ph-H), 7.51 (s, 0.57H, Ph-H), 7.55 (s, 0.43H, Ph-H) ppm. $^{13}$C{$^1$H} NMR ($C_6D_6$): 15.15, 15.80, 16.14, 16.81, 17.34, 17.70, 17.97, 21.07, 28.13, 43.76, 122.53, 122.60, 123.98, 124.03, 125.98, 126.57, 130.04, 130.20, 132.37, 134.28, 134.35, 136.96, 137.84, 138.59, 138.63, 139.38, 139.83, 142.27, 143.80, 143.96, 1585.80, 155.89 ppm.

COMPARATIVE EXAMPLE 1

(tetramethylcyclopentadienyl)titanium trichloride

The titanium metal compound was obtained from US Boulder Scientific Co and used for ethylene copolymerzation.

COMPARATIVE EXAMPLE 2 iso-propyllidene(cyclopentadienyl)(9-fluorenyl)zirconium dichloride

The zirconium metal compound was obtained from US Boulder Scientific Co. and used for ethylene homo copolymerization.
Ethylene Copolymerization

EXAMPLE 25 high pressure ethylene and 1-octene copolymerization 1.0 L of toluene solvent and 1-octene (fixed at 0.8 M) were added to a 2 L autoclave reactor. Then, temperature in the reactor was preheated to 90° C. and at the same time, the reactor was filled with ethylene such that the ethylene pressure in the reactor was 6 bar. A 25 mL catalyst storage tank was sequentially filled with 5.0 micromole of titanium compound that had been treated with 125 micromole of triisobutylaluminum compound and 25 micromole of trityl tetrakis (pentafluorophenyl)borate cocatalyst. At this time, ethylene pressure (13 bar) was applied to the catalyst tank and copolymerzation was performed for 10 minutes. Then, the residual ethylene gas was removed and excess ethanol was added to the polymer solution to cause precipitation. The obtained polymer precipitate was washed two to three times with ethanol and acetone, respectively. The washed polymer was dried in a vacuum oven at 80° C. for 12 hours or more.

Properties Measurement (Weight, Activity, Melt Index, Melting Point, and Density)

A melt index (MI) of a polymer was measured using ASTM D-1238 (Condition E, 190° C., 2.16 Kg weight). A melting point ($T_m$) of the polymer was a Differential Scanning Calorimeter (DSC) 2920 produced by TA Co. That is, the DSC curve of the polymer was obtained by increasing the temperature to 200° C., maintaining at 200° C. for 5 minutes, decreasing to 30° C., and then increasing again. The summit of the DSC curve corresponds to a melting point. At this time, the increase and decrease rates of the temperature were 10° C./min, and the melting point was obtained in a second temperature increase period.

In order to measure the density of the polymer, a sample that had been treated with 1,000 ppm of an antioxidant was formed into a sheet having a thickness of 3 mm and a diameter of 2 cm by a 180° C. press mold, and then the prepared sheet was cooled to 10° C./min. The cooled sheet was measured using a mettler scale.

EXPERIMENTAL EXAMPLE 1

Copolymerization of ethylene and 1-octene

Various properties of copolymers prepared according to Example 25 using transition metal complexes prepared according to Examples 19, 20, 23, and 24 and Comparative Example 1. The results are shown in Table 1.

TABLE 1

| Complex used | Polymer weight (g) | Activity (Kg/mmol-Ti hr) | Melt Index[a] (g/10min) | Melting Point (°C.) | Density (g/cc) |
|---|---|---|---|---|---|
| Example 19 | 63.59 | 76.31 | 1.63 | 62.2 | 0.863 |
| Example 20 | 84.51 | 101.41 | 6.25 | 60.3 | 0.860 |
| Example 23 | 8.21 | 9.85 | Not measurable | Has not been measured | 0.850 |
| Example 24 | 9.99 | 11.99 | Not measurable | Has not been measured | 0.877 |
| Comparative Example 1 | 15.6 | 18.7 | 0.91 | 57.5, 97.1 | 0.872 |
| Comparative Example 2 | 112.1 | 134.6 | 66.4 | 98.5 | 0.910 |

[a]$I_2$ value

As shown in Table 1, compared to the catalyst complex of Comparative Example 1, the catalyst complexes prepared according to Examples 19, 20, 23, and 24 showed higher copolymerization activity. In addition, a polymer that was synthesized using the catalyst complexes prepared according to Examples 19, 20, 23, and 24 had higher molecular weight and lower density. Compared to the catalyst complex of Comparative Example 2, the catalyst complexes prepared according to Examples 19, 20, 23, and 24 in which a metal atom is not crosslinked by a bridge showed somewhat lower activity but when used to synthesize a copolymer, the synthesized copolymer showed higher molecular weight and lower density.

A transition metal complex according to the present invention has a novel structure in which an imino phenyl group is not cross-linked to a metal atom and directly introduced to a cyclopentadiene (Cp) ring. A catalyst composition including the transition metal complex is used to produce a polyolefin copolymer having a very low density less than 0.910 g/cc.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A transition metal complex of Formula 1:

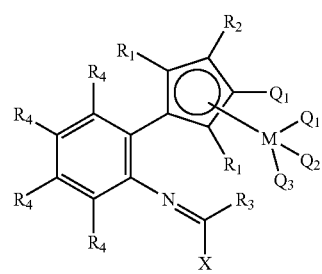

(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;

$R_4$ is each independently a hydrogen atom; a halogen radical; or a C1-C20 alkyl or aryl radical, wherein two $R_4$ can be connected to form a fused ring structure;

$R_3$ is hydrogen atom; a C1-C20 alkyl or aryl radical; or a C1-C20 alkoxy or aryloxy radical;

M is a transition metal of Group 4;

$Q_1$, $Q_2$, and $Q_3$ are each independently a halogen radical; an amino radical; a C1-C20 alkyl or aryl amido radical; or a C1-C20 alkyl, alkenyl, aryl, alkylaryl, or arylalkyl radical; and X is halogen.

2. The transition metal complex of claim 1, being represented by one of the formulae below:

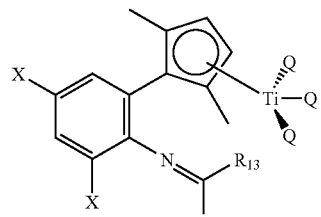

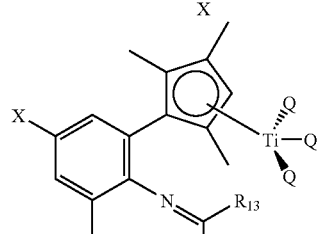

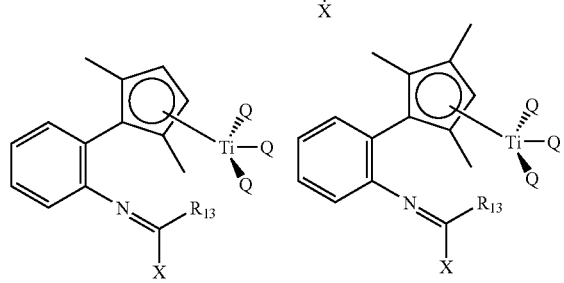

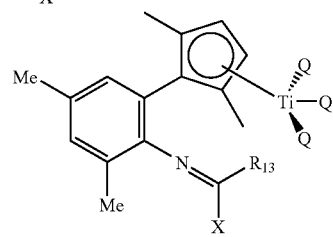

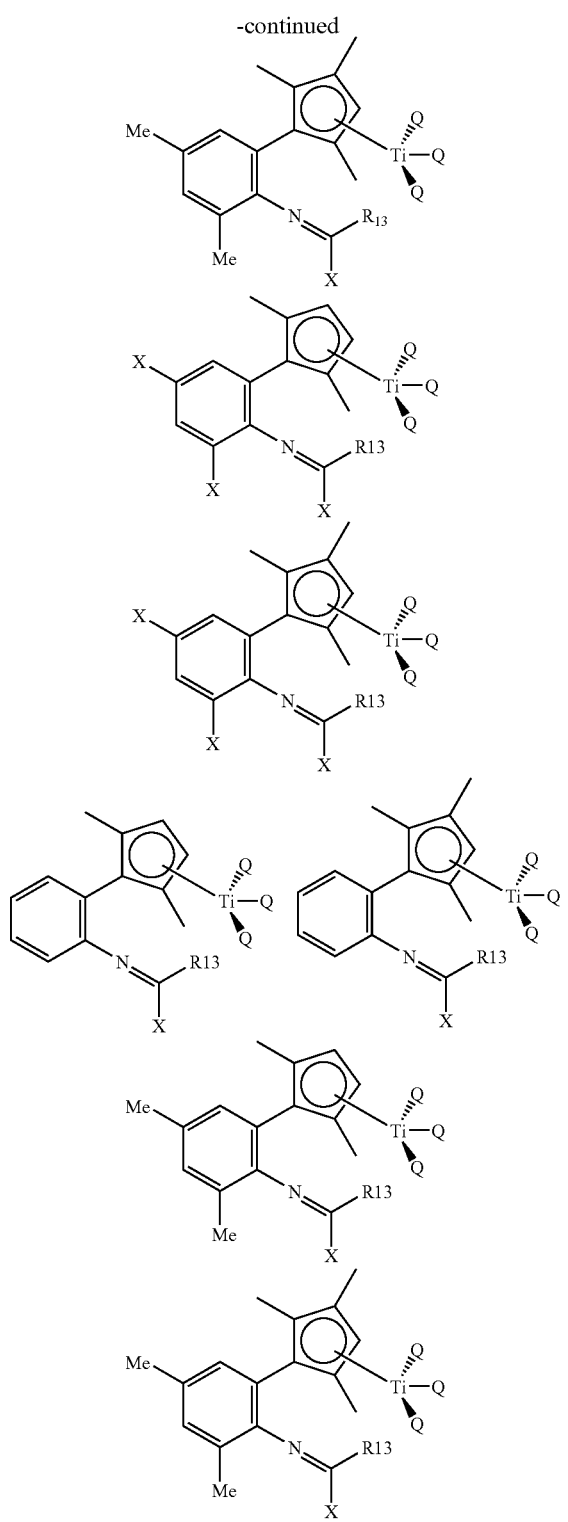

where R₁₃ is hydrogen, methyl, a t-butyl or t-butoxy radical, X is halogen, and Q is alkyl, halogen, or amino radical.

3. A method of synthesizing a transition metal complex represented by Formula 1, the method comprising:
synthesizing a compound of Formula 4 by reacting a boronic acid compound of Formula 2 with a 2-bromoaniline compound of Formula 3;

synthesizing a compound of Formula 5 by reacting the compound of Formula 4 with $R_1Li$ and then adding an acid thereto;

synthesizing a compound of Formula 6 by reacting the compound of Formula 5 with $R_5X$ where X is halogen; and synthesizing a complex of Formula 1 by reacting the compound of Formula 6 with a compound of Formula 7 and then adding $(CH_3)_nSiX_{4-n}$ where X is halogen and n is 0, 1, 2, or 3 thereto:

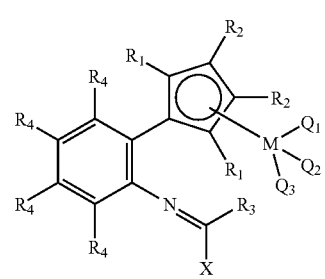

(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of a Group 14 metal substituted with hydrocarbyl, wherein $R_1$ and $R_2$ can be connected by an alkylidine radical that contains a C1-C20 alkyl or aryl radical to form a ring;

$R_4$ is a hydrogen atom; a halogen radical; or a C1-C20 alkyl or aryl radical, wherein two $R_4$ can be connected to form a fused ring structure;

$R_3$ is hydrogen atom; a C1-C20 alkyl or aryl radical; or a C1-C20 alkoxy or aryloxy radical;

M is a transition metal of Group 4;

$Q_1$, $Q_2$, and $Q_3$ are each independently a halogen radical; a C1-C20 alkyl or aryl amido radical; or a C1-C20 alkyl, alkenyl, aryl, alkylaryl, or arylalkyl radical; and X is halogen;

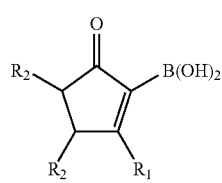

(2)

where $R_1$ and $R_2$ are described above;

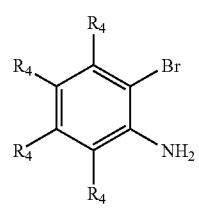

(3)

where $R_4$ is described above;

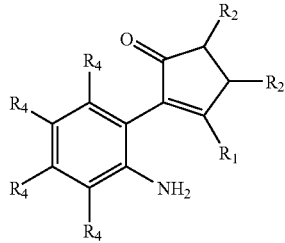
(4)

where $R_1$, $R_2$, and $R_4$ are described above;

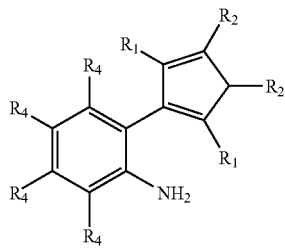
(5)

where $R_1$, $R_2$, and $R_4$ are described above;

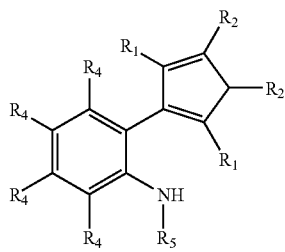
(6)

where $R_1$, $R_2$, and $R_4$ are described above, $R_5$ is a C1-C20 alkyl carbonyl, aryl carbonyl, or silyl carbonyl radical; or a C1-C20 alkyl carboxy, or aryl carboxy radical; and $$M(N(R_6)_2)_4 \quad (7)$$

where $R_6$ is a C1-C20 alkyl or aryl radical.

4. A method of synthesizing a transition metal complex represented by Formula 1, the method comprising:
synthesizing a compound of Formula 4 by reacting a boronic acid compound of Formula 2 with a 2-bromoaniline compound of Formula 3;
reacting the compound of Formula 4 with $R_5X$ where X is halogen to obtain a reaction product;
synthesizing a compound of Formula 6 by reacting the reaction product with $R_1Li$ and then adding an acid thereto; and
synthesizing a complex of Formula 1 by reacting a compound of Formula 6 with a compound of Formula 7 and then adding $(CH_3)_n SiX_{4-n}$ where X is halogen and n is 0, 1, 2, or 3 thereto:

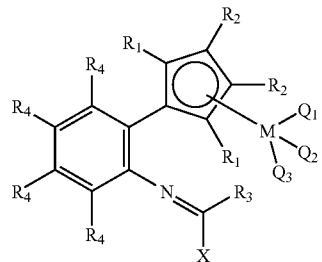
(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;
is a hydrogen atom; a halogen radical; or a C1-C20 alkyl or aryl radical, wherein two $R_4$ can be connected to form a fused ring structure;
is hydrogen atom; a C1-C20 alkyl or aryl radical; or a C1-C20 alkoxy or aryloxy radical;
M is a transition metal of Group 4;
$Q_1$, $Q_2$, and $Q_3$ are each independently a halogen radical; a C1-C20 alkyl or aryl amido radical; or a C1-C20 alkyl, alkenyl, aryl, alkylaryl, or arylalkyl radical; and
X is halogen;

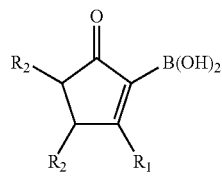
(2)

where $R_1$ and $R_2$ are described above;

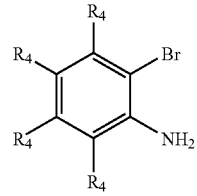
(3)

where $R_4$ is described above;

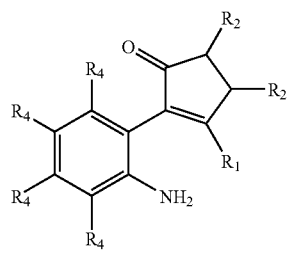
(4)

where $R_1$, $R_2$, and $R_4$ are described above;

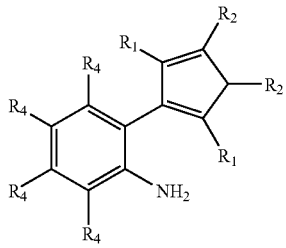
(5)

where $R_1$, $R_2$, and $R_4$ are described above;

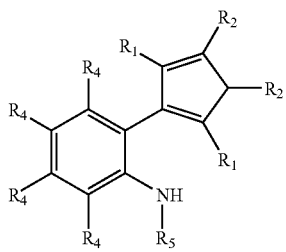
(6)

where $R_1$, $R_2$, and $R_4$ are described above, $R_5$ is a C1-C20 alkyl carbonyl, aryl carbonyl, or silyl carbonyl radical; or a C1-C20 alkyl carboxy, or aryl carboxy radical; and $$M(N(R_6)_2)_4 \tag{7}$$

where $R_6$ is a C1-C20 alkyl or aryl radical.

5. A catalyst composition comprising:
the transition metal complex of Formula 1; and
at least one cocatalyst compound selected from the group consisting of compounds represented by Formulae 8 through 10:

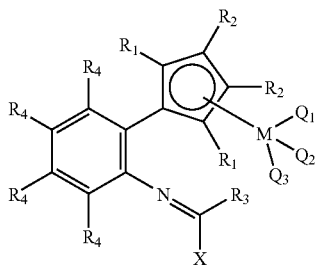
(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;
$R_4$ is a hydrogen atom; a halogen radical; or a C1-C20 alkyl or aryl radical, wherein two $R_4$ can be connected to form a fused ring structure;
$R_3$ is hydrogen atom; a C1-C20 alkyl or aryl radical; or a C1-C20 alkoxy or aryloxy radical;
M is a transition metal of Group 4;
$Q_1$, $Q_2$, and $Q_3$ are each independently a halogen radical; a C1-C20 alkyl or aryl amido radical; or a C1-C20 alkyl, alkenyl, aryl, alkylaryl, or arylalkyl radical; and
X is halogen;

$$-[Al(R_7)-O]_a- \tag{8}$$

where $R_7$ is a halogen radical; a C1-C20 hydrocarbyl radical; or a C1-C20 hydrocarbyl radical substituted with halogen, a is an integer of 2 or greater;

$$D(R_7)_3 \tag{9}$$

where D is aluminum or boron, $R_7$ is described above; and $$[L-H]^+[Z(A)_4]^-, \text{ or } [L]^+[Z(A)_4]^- \tag{10}$$

where L is a neutral Lewis base, H is a hydrogen atom; Z is an element of Group 13; and A is each independently a C6-C20 aryl or alkyl radical in which at least one hydrogen atom is substituted with halogen or a C1-C20 hydrocarbyl, alkoxy, or phenoxy radical.

6. A method of preparing a catalyst composition, the method comprising:
contacting the transition metal complex of Formula 1 with the compound of one of Formulae 8 and 9, thereby obtaining a mixture; and
adding a compound of Formula 10 to the mixture:

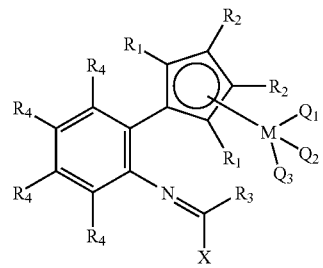
(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;
$R_4$ is a hydrogen atom; a halogen radical; or a C1-C20 alkyl or aryl radical, wherein two $R_4$ are connected to form a fused ring structure;
$R_3$ is hydrogen atom; a C1-C20 alkyl or aryl radical; or a C1-C20 alkoxy or aryloxy radical;
M is a transition metal of Group 4;
$Q_1$, $Q_2$, and $Q_3$ are each independently a halogen radical; a C1-C20 alkyl or aryl amido radical; or a C1-C20 alkyl, alkenyl, aryl, alkylaryl, or arylalkyl radical; and
X is halogen;

$$-[Al(R_7)-O]_a- \tag{8}$$

where $R_7$ is a halogen radical; a C1-C20 hydrocarbyl radical; or a C1-C20 hydrocarbyl radical substituted with halogen, a is an integer of 2 or greater;

$$D(R_7)_3 \tag{9}$$

where D is aluminum or boron, $R_7$ is described above; and $$[L-H]^+[Z(A)_4]^-, \text{ or } [L]^+[Z(A)_4]^- \tag{10}$$

where L is a neutral Lewis base, H is a hydrogen atom; Z is an element of Group 13; and A is each independently a C6-C20 aryl or alkyl radical in which at least one hydrogen atom is substituted with halogen or a C1-C20 hydrocarbyl, alkoxy, or phenoxy radical.

7. The method of claim 6, wherein the mole ratio of the transition metal complex of Formula 1 to the compound of Formula 8 or Formula 9 is in the range of 1:2 to 1:5000 and the mole ratio of the transition metal complex of claim 1 to the compound of Formula 10 is in the range of 1:1 to 1:25.

8. A method of synthesizing an olefin polymer, comprising contacting the catalyst composition of claim 5 with a monomer.

9. The method of claim 8, wherein the monomer comprises at least one monomer selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-icosene.

* * * * *